United States Patent [19]

Girijavallabhan et al.

[11] Patent Number: 5,459,144
[45] Date of Patent: Oct. 17, 1995

[54] PHARMACEUTICALLY ACTIVE COMPOUNDS

[75] Inventors: Viyyoor M. Girijavallabhan, Parsippany; Ashit K. Ganguly, Upper Montclair; Patrick A. Pinto, Mine Hill; Richard W. Versace, Wanaque, all of N.J.

[73] Assignee: Schering Corporation, Kenilworth, N.J.

[21] Appl. No.: 169,809

[22] Filed: Dec. 17, 1993

Related U.S. Application Data

[60] Division of Ser. No. 809,474, Dec. 18, 1991, Pat. No. 5,272,167, which is a continuation-in-part of Ser. No. 376,476, Jul. 7, 1989, abandoned, which is a continuation-in-part of Ser. No. 940,125, Dec. 10, 1986, Pat. No. 4,851,423.

[51] Int. Cl.$^6$ ............... A61K 31/505; A61K 31/44; A61K 31/425; A61K 31/415; C07D 487/00; C07D 405/12; C07D 471/02; C07D 211/70

[52] U.S. Cl. .............. 514/269; 514/258; 514/261; 514/266; 514/277; 514/300; 514/348; 514/369; 514/378; 514/383; 514/394; 514/395; 514/397; 514/399; 514/427; 514/473; 544/256; 544/262; 544/264; 544/310; 544/314; 544/277; 544/374; 544/379; 546/123; 546/296; 546/339; 548/186; 548/251; 548/252; 548/240; 548/267.8; 548/268.6; 548/304.4; 548/306.4; 548/312.7; 548/315.4; 548/341.1; 549/476

[58] Field of Search ............... 544/310; 514/269

[56] References Cited

U.S. PATENT DOCUMENTS 4,540,703  9/1985  Uchida et al. .................. 514/381
4,725,619  2/1988  Chakraborty et al. .................. 514/442
4,728,668  3/1988  Chakraborty et al. .................. 514/464
4,839,369  6/1989  Youssefyeh et al. .................. 514/314

FOREIGN PATENT DOCUMENTS 49264   5/1986   Australia .
60240   7/1986   Australia .
56430  10/1986   Australia .
56398  10/1986   Australia .
54424  11/1986   Australia .
71993  10/1987   Australia .
200101 10/1986   European Pat. Off. .
192405  7/1984   New Zealand .
199953  7/1984   New Zealand .
192941 10/1984   New Zealand .
207412  1/1987   New Zealand .

Primary Examiner—Cecilia Tsang
Attorney, Agent, or Firm—Eric S. Dicker; John J. Maitner; Matthew Boxer

[57] ABSTRACT

The invention relates to compounds of the formula $$Z-X-Q-Y-W \quad Z-X-Q-Y-W'-Y-Q-X-Z$$
$$\text{(I)} \qquad\qquad \text{(II)}$$

wherein Z, X, Q, Y, W, and W' are as described herein.

These compounds have antiviral activity, and certain of these compounds have antiinflammatory activity and are PAF inhibitors.

3 Claims, No Drawings

PHARMACEUTICALLY ACTIVE COMPOUNDS

This is a division of application Ser. No. 07/809,474, filed Dec. 18, 1991, U.S. Pat. No. 5,272,167, which is a continuation-in-part of U.S. application Ser. No. 07/376,476 filed Dec. 7, 1989 now abandoned, which in turn is a continuation-in-part of U.S. application Ser. No. 06/940,125 filed Dec. 10, 1986, U.S. Pat. No. 4,851,423.

This invention relates to compounds with pharmaceutical activity, i.e. antiviral, antiinflammatory and platelet activating factor inhibition, their pharmaceutically acceptable salts and solvates and pharmaceutical compositions containing the active compounds.

Arildone, a compound represented by the formula

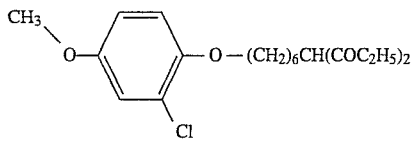

is active in vitro against herpes virus and polio virus, but is only marginally active against rhinoviruses. Diana et al., J. Med. Chem. 28, 748 (1985) prepared some alkyl-substituted isoxazole analogs of arildone in an attempt to prepare compounds with broad spectrum activity against picornaviruses. Some of the compounds were active against both rhinovirus type 2 and poliovirus type 2. However, there is no indication that any of the Diana et al. compounds have activity as antiinflammatories or as platelet activating factor inhibitors. Many of the compounds of this invention possess such activity. The following publications are also cited: EPA 86043; U.S. Pat. No. 4,540,703; EPA 49060; U.S. Pat. No. 3,190,888; EPA 112292; EPA 218543 and EPA 274867 as well as J. Med. Chem 28, (1985) pages 748–752.

The compounds of this invention are represented by the following structural formulas I and II $$Z-X-Q-Y-W \quad\quad Z-X-Q-Y-W'-Y-Q-X-Z$$
$$\text{(I)} \quad\quad\quad\quad\quad\quad \text{(II)}$$

pharmaceutically acceptable acid addition, basic addition, and quarternary amine salts thereof and pharmaceutically acceptable solvates thereof, wherein each Z is independently tertiary butyl; phenyl; naphthyl; adamantanyl; substituted phenyl, wherein the substituents are one or more of halogen, lower alkoxy, phenoxy, nitrile, nitro, phenylsulfonyl, loweralkylsulfonyl, oxazol-2-yl, lower alkanoyl, benzoyl, lower alkoxycarbonyl, lower alkyl, phenyl, lower alkylthio, phenylaminothiocarbonyl, lower alkylaminothiocarbonyl, hydroxyiminoloweralkyl, hydroxyloweralkyl or carbamyl; or 4 to 6 membered unsubstituted or substituted hetrocyclic ring containing at least one nitrogen in the ring with the remaining members of the ring being at least one carbon, and optionally sulfur or oxygen wherein the substituents are one or more of —COOH, $CH_2OH$, lower alkyl, loweralkylcarbonyl or aryl lower alkyl;

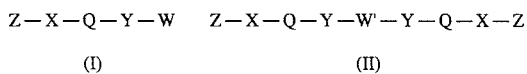

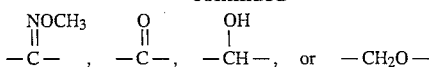

each Q is independently a divalent substituted or unsubstituted, straight or branched chain lower alkanediyl, loweralkanediyl-cycloalkanediyl-loweralkanediyl, lower alkenediyl, lower alkynediyl, phenylene, dihydrofurandiyl, loweralkanediyl-dihydrofurandiyl-loweralkanedily, tetrahydrofurandiyl, tetrahydropyrandiyl, loweralkanediyl-tetrahydropyrandiyl-loweralkanediyl, loweralkanediyl-tetrahydrofurandiyl-loweralkanediyl wherein the substituents are one or more of hydroxy, ketalized adjacent hydroxys (see, for example, Example 91), epoxy, fluorine, chlorine, azide, or amino;

W is a monovalent substituted or unsubstituted aryl group, wherein the substituents on the aryl group are as defined above for Z wherein Z is substituted phenyl, or an unsubstituted or substituted heterocyclic single or fused ring containing from 4 to 10 ring atoms, at least one hetero atom of which is a nitrogen atom and the remaining ring atoms being at least one carbon and optionally sulfur or oxygen, wherein the substituents on the heterocyclic ring are one or more of hydroxy, oxo, amino, carbamoyl, carboxyl, nitrile, nitro, lower alkyl, loweralkoxycarbonyl, halogen, sulfamyl, loweralkoxycarbonylloweralkyl, loweralkythio, lower alkoxy, hydroxy loweralkyl, amino loweralkyl, carboxy loweralkyl, guanidino, thioureido, lower alkyl sulfonylamino, aminocarbonylloweralkyl, allyloxycarbonylmethyl or carbamoyloxyloweralkyl, with the proviso that W cannot be substituted or unsubstituted isoxazolyl, and with the further proviso that when Z is 2-chloro-4-methoxyphenyl, X is —O—, Q is $C_5$–$C_7$ alkanediyl and Y is a bond, W is not imidazolyl substituted at positions 2, 4 and 5 with 1–3 substituents independently selected from the group consisting of hydrogen, hydroxyloweralkyl, nitro, loweralkoxycarbonyl, lower alkyl and amino methylene;

W' is divalent W.

The invention also includes pharmaceutical compositions containing pharmaceutically effective amounts of a compound of formula I or formula II as well as method of treating virus infections, inflammation and inhibiting platelet activating factor using the appropriate pharmaceutical compositions.

As used herein "lower alkyl" alone or in combined form, e.g. "lower alkoxy" or "loweralkanediyl", means straight or branched chain alkyl groups of from 1 to 10 carbon atoms, e.g. methyl, ethyl, propyl, isopropyl, butyl, t-butyl, pentyl, neopentyl, hexyl and the like.

The heterocyclics at Z and W are monovalently bonded to X and Y respectively by a hetero atom, preferably nitrogen, or by a carbon atom. The heterocyclics at W' preferably have two nitrogens, each of which is bonded to a separate —Y—Q—X—Z moiety.

Heterocyclic groups within the scope of this invention for Z are, for example, imidazolyl (such as imidazol-1-yl, imidazol-2-yl, imidazol-4-yl, and imidazol-5-yl), dihydrothiazolyl (such as 4, 5-dihydrothiazol-2-yl), tetrazol (such as tetrazol-5-yl, tetrazol-1-yl, and tetrazol-2-yl), pyridinyl (such as pyridin-2-yl), triazolyl (such as 1, 2, 4-triazol-1-yl), tetrahydro-pyrimidinyl (such as 1, 2, 3, 4-tetrahydropyrimidin-1-yl), dihydro-oxazolyl (such as 4, 5-dihydro-oxazol-2-yl), pyrrolidinyl (such as pyrrolidin-1-yl), pyrazolyl (such as pyrazol-1-yl and pyrazol-2-yl), morpholinyl, azetidinyl, and oxetanyl. All possible attachment positions of the above heterocyclic groups are within the scope of this invention.

Heterocyclic groups within the scope of this invention for W are, for example, all those listed above for Z and, in addition, fused ring compounds, for example benzamidazolyl (such as benzimidazol-1-yl and benzimidazol-2-yl), naphthyridinyl (such as naphthyridin-1-yl), purine (such as purine-9-yl and purine-7-yl), and quinolinyl.

Heterocyclic groups within the scope of this invention for W' are all those listed above for Z and W, but being divalent. For example, if W' were tetrahydropyrimidinyl, it could be 1, 2, 3, 4-tetrahydro-pyrimidin-1, 3-diyl. W' as a benzimidazolyl group could be, for example benzimidazol-1,3-diyl. In other words, to obtain a possible W' group from the groups listed for Z and W, the "yl" suffix in the Z and W radical is replaced by "diyl".

"Aryl" as used herein refers to phenyl and naphthyl.

"Halogen" as used herein means chlorine, fluorine, bromine or iodine with chlorine or fluorine preferred.

"Cycloalkane", alone or in combined form, means a 4, 5, 6 or 7 membered saturated carbocyclic ring.

"Lower alkene", alone or in combined form, means a 2 to 10 carbon branched or straight chain alkene group.

"Lower alkyne", alone or in combined form, means a 2–10 carbon branched or straight chain alkyne group.

"Pharmaceutically acceptable salts" as used herein means acid addition salts formed from mineral acids such as hydrochloric, hydrobromic, phosphoric or sulfuric acids, or formed from organic carboxylic or sulfonic acids such as trifluoroacetic, para-toluene, sulfonic, maleic, acetic, citric, oxalic, succinic, benzoic, tartaric, fumaric, mandelic, ascorbic and malic acids, or quaternary salts prepared from such organic halides as methyl iodide, ethyl iodide, benzyl chloride and the like, although all pharmaceutically acceptable quaternary salts are contemplated. Basic addition salts are also within the scope of this invention.

The above salts are made by conventional means in the art, e.g. reaction of the compound with the appropriate acid, organic halide, or base.

The preferred salt is the hydrochloride salt.

"Hydroxy protecting group" as used herein means any known hydroxy protecting group which is removed by conventional reactions which do not adversely affect the compounds produced. Typical suitable hydroxy protecting groups are t-butyldimethylsilyl (TBDMS) or tetrahydropyranyl.

The compounds of this invention have been found to be active against ether-resistant RNA viruses, i.e. picornaviruses which includes enteroviruses and rhinoviruses. The enteroviruses include poliovirus, coxsackieviruses and echoviruses. Rhinoviruses include those viruses associated with the common cold and certain other respiratory ailments. Over one hundred serotypes are identified. Although the compounds of this invention are not active against all the rhinoviruses, they are active against a large number of them including rhinovirus 2. The compounds of this invention are also active against the enteroviruses such as poliovirus 2, coxsackieviruses A and B3, and ECHO. In addition, the compounds of this invention are active against certain DNA viruses such as herpesvirus and cytomegalovirus.

In vitro antiviral activity of the compounds of this invention was determined by an assay which measures the inhibitory effect a compound has on picornavirus RNA synthesis: the extent that a test compound inhibits viral RNA synthesis is a measure of the ability of the compound to inhibit viral infectivity. The assay involves comparison of the incorporation of $^3$H-uridine into picornavirus RNA in the presence and absence (i.e., a non-treated control) of the test compound and determination of the percentage of inhibition. To ensure that the maximum amount of $^3$H-uridine is incorporated into viral RNA rather than cellular RNA, actinomycin D is used to inhibit cellular RNA synthesis. Since the synthesis of picornavirus RNA is dependent on an RNA template rather than a DNA template, viral replication is not affected by actinomycin D. In tests against coxsackievirus B3, $IC_{50}$ values of active compounds of this invention varied from about 2 to about 8 micrograms/ml; against cosackievirus A21, values were from less than about 5 to about 20; against poliovirus 2, values were about 2 to about 9; and against rhinovirus 14 values were about 1 to about 18 micrograms/ml. (The $IC_{50}$ value is the concentration of test compound in micrograms per ml which results in a 50% decrease in viral RNA synthesis.)

Compounds of this invention were also tested in a pre-mix plaque reduction assay (See U.S. Ser. No. 06/940,125, filed Dec. 10, 1986) against echovirus 9, wherein the $IC_{50}$ values ranged from about 7 to about 18 micrograms/ml.

Of the antiviral compounds within the scope of formulas I and II, those which form water soluble acid addition salts are orally absorbable, show good tissue levels and serum stability.

The preferred antiviral compounds of this invention are those represented by the following formula III

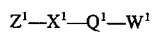   III and pharmaceutically acceptable acid addition salts thereof, wherein $Q^1$ is lower alkanediyl of 5, 6 or 7 carbons; lower alkynediyl of 6, 7 or 8 carbon atoms; all possible isomers of methylcyclohexylmethyl; tetrahydrofurandiyl, or $(C_1-C_2)$loweralkanediyl-tetrahydrofurandiyl-$(C_1-C_2)$-loweralkanediyl, wherein the tetrahydrofuran ring is substituted with 0–2 hydroxy groups;

$W^1$ is unsubstituted or substituted imidazo-1-yl, purin-9-yl or imidazo-2-yl, wherein said substituents are one or more of loweralkyl, hydroxy loweralkyl, nitro, lower alkoxycarbonyl, carboxymethyl, aminocarbonylmethyl;

$X^1$ is a bond,

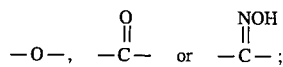

and $Z^1$ is

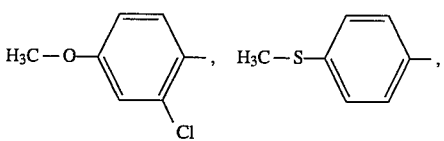

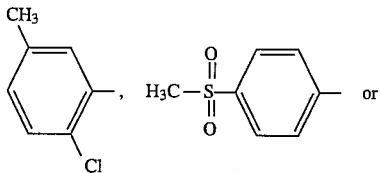

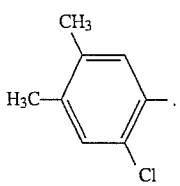

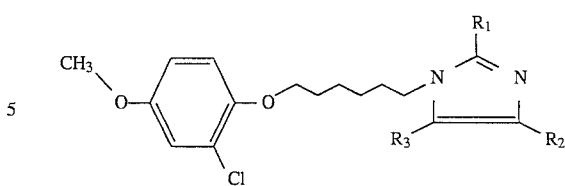

The preferred acid addition salt is the hydrochloride.

Certain compounds of this invention have been found to display activity in animal models of inflammation, Thus, in a reverse passive Arthus reaction in rats, the compounds were orally active when administered at dosages of from 25 to 100 mg/kg and in the adjuvant induced arthritis test in rats were orally active.

The reverse passive Arthus test evaluates test compounds for activity against an immune complex, cell-mediated inflammatory reaction. In the performance of the test, rats previously fasted for 24 hours are dosed with the test compound, then after one hour are lightly anesthesized and injected (iv) with 1.0 mg bovine serum albumin (BSA) in 0.1 ml sterile saline. Then the rats are injected intrapleurally with 0.1 ml sterile saline containing 100 micrograms of antibody protein to bovine serum albumin.

Four hours after challenge, the rats are sacrificed and pleural cavity transudate is removed and the volume recorded. The pleural cavity is then washed with 3 ml of cold saline and the wash is removed and added to the original transudate. After being treated with an anticlot agent or EDTA, the transudate is cooled on ice and the volumes of the test transudate and control transudate are adjusted to 5.5 ml with saline and their white blood cell counts are determined on a Z1 Coulter Counter. The differences between transudate volume (a measure of edema) and total white blood cell counts (a measure of neutrophil accumulation) between the controls and drug treated groups is a measure of the drugs antiinflammatory activity. These effects are stated as a percent inhibition or reduction in neutrophil count and transudate volume.

The adjuvant induced arthritis test in rats evaluates the effect of a drug on an immune mediated model of chronic inflammation. In the performance of the test, animals (rats) are dosed orally with drugs at a volume of 1 ml per 100 grams of body weight. The drug concentration is varied for different test dosages. The rats are dosed with the test compound one hour prior to sensitization with an adjuvant. The adjuvant used in this test model is heat killed mixed *M. tuberculosis* homogenized in paraffin oil. Controls are given the methylcellulose vehicle alone.

The adjuvant is injected into the subplantar region of the left hind paw, immediately thereafter the volumes of the left and right hind paws are measured with a plethysmograph. Injected paw volumes are measured after 24 hours and then 21 days later. The contralateral hind paw is only measured 21 days later. The differences in paw volumes between the first and last measurements are related to the degree of inflammation. Antiinflammatory drugs reduce these differences.

The compounds of this invention which exhibit antiinflammatory activity are those with an imidazo-1-yl or lower alkyl substituted imidazo-1-yl at the W position of formula I.

Preferred antiinflammatory compounds of this invention are represented by the following compound IV and pharmaceutically acceptable acid addition salts thereof, wherein $R_1$, $R_2$ and $R_3$ are each independently hydrogen, hydroxyloweralkyl or lower alkyl, with the proviso that when one of $R_2$ and $R_3$ is lower alkyl, the other is hydrogen.

Certain of the compounds of this invention have been found to display platelet-activating factor (PAF) antagonism. PAF has been shown to be involved in the pathophysiology of various allergic and inflammatory diseases. It is an important mediator of such processes as platelet aggregation, smooth muscle contraction, especially lung tissue, vascular permeability and neutrophil activation. Furthermore, recent evidence implicates PAF as the underlying factor involved in airway hyperreactivity. As such, PAF is implicated in diseases such as asthma (bronchoconstriction and pulmonary edema) and inflammation.

Antagonists or inhibitors of PAF, such as the compounds of this invention, would therefore be of use whenever PAF is a factor in the disease or disorder. This includes allergic diseases such as asthma, adult respiratory distress syndrome and urticaria, and inflammatory diseases such as rheumatoid arthritis and osteoarthritis.

In the in vivo PAF Induced Bronchiospasm in Guinea Pigs, compounds of this invention exhibit $IC_{50}$ values of from about 3 to about 60 mg per kg. In the in vitro PAF Antagonism Assay, compounds of this invention show an inhibition of PAF activity from about 20 to 100% at varying concentrations.

The PAF Induced Bronchiospasm in Guinea Pigs assay is conducted as follows:

Non-sensitized guinea pigs were fasted overnight, and the following morning were anesthetized with 0.9 ml/kg i.p. of dialurethane (0.1 gm/ml of diallylbarbituric acid, 0.4 gm/ml of ethylurea and 0.4 gm/ml of methane). The trachea was cannulated and the animals were ventilated by a Harvard rodent respirator at 55 strokes/min with a stroke volume of 4 ml. A side arm to the tracheal cannula was connected to a Harvard pressure transducer to obtain a continuous measure of intratracheal pressure, which was measured on a Harvard polygraph. The jugular vein was cannulated for the administration of compounds. The animals were challenged i.v. with PAF (0.4 µg/kg in isotonic saline containing 0.25% BSA) and the peak increase in inflation pressure that occurred within 5 min. after challenge was recorded. Test compounds were administered either orally (2 hours prior to PAF as a suspension in 0.4% methyl cellulose vehicle) or intravenously (10 minutes prior to PAF as a solution in DMSO).

The effect of compounds on the bronchiospasm is expressed as a percent inhibition of the peak increase in intratracheal pressure compared to the peak increase in the control group. The $IC_{50}$ is the dosage in mg/kg required to obtain a 50% inhibition.

The in vitro PAF Antagonism Assay as conducted as follows:

Platelet-activating factor (PAF) causes aggregation of platelets in a receptor-mediated mechanism. Therefore, PAF-induced platelet aggregation provides a simple and convenient assay to screen compounds for PAF antagonism.

Preparation of platelet-rich plasma (PRP)

Human blood (50 ml) is collected from healthy male donors in an anticoagulant solution (5 ml) containing sodium citrate (3.8%) and dextrose (2%). Blood is centrifuged at 110× g for 15 min. and the supernatant (PRP) carefully transferred into a polypropylene tube. Platelet-poor-plasma (PPP) is prepared by centrifuging PRP at 12,000× g for 2 min. (Beckman Microfuge B). PRP is used within 3 hours of drawing the blood.

Platelet Aggregation Assay

When an aggregating agent such as PAF is added to PRP, platelets aggregate. An aggregometer quantifies this aggregation by measuring and comparing light (infrared) transmission through PPP and PRP. The aggregation assays performed on the compounds of this invention are performed using a dual-channel aggregometer (Model 440, Chrono-Log Corp., Havertown, Pa.). PRP (0.45 ml) in aggregometer curettes is continually stirred (37° C.). Solutions of test compounds or vehicle are added to the PRP, and after incubation for 2 min., 10–15 µl aliquots of PAF solution are added to achieve a final concentration of $1-5\times10^{-8}M$. Incubations are continued until the increase in light transmission reaches a maximum (usually 2 min.). Values for inhibition are calculated by comparing maximal aggregation obtained in the absence and the presence of the test compound and expressed as percent inhibition. For each experiment, a standard PAF antagonist such as alprazolam is used as a positive internal control.

Preferred PAF antagonist compounds of this invention are represented by the following formula V:

$$Z^2-X^2-Q^2-Y^2-W^2 \qquad V$$

pharmaceutically acceptable acid addition salts or quaternary amine salts thereof, wherein $Z^2$ is phenyl; substituted phenyl wherein the substituents are independently one or more of halogen, loweralkythio, loweralkylsulfonyl, lower alkoxy, oxazol- 2-yl, phenoxy; imidazol-1-yl; lower alkyl substituted imidazol-1-yl; or tert-butyl;

$X^2$ is a bond,

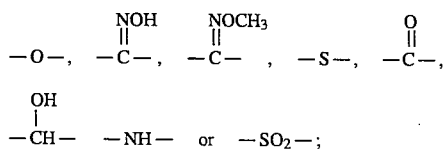

$Q^2$ is lower alkanediyl of 5, 6 or 7 carbon atoms optionally substituted by —OH; loweralkynediyl of 6–8 carbon atoms; methylcyclohexylmethyl; tetrahydrofurandiyl; or $(C_1-C_2)$loweralkanediyl-tetrahydrofurandiyl-$(C_1-C_2)$-loweralkanediyl, wherein the tetrahydrofuran ring is substituted by 0–2 hydroxy groups;

$Y^2$ is a bond; and $W^2$ is imidazol-1-yl; substituted imidazol-1-yl wherein the substituents are independently one or more of loweralkyl, hydroxy loweralkyl, aminoloweralkyl and lower alkoxycarbonyl; imidazol-2-yl; imidazol-4-yl; imidazol-5-yl; substituted imidazol-2-yl, -4-yl or -5-yl, wherein the substituents are independently one or more of lower alkyl, and allyloxycarbonylmethyl; pyrrolidin-1-yl; benzimidazol-1-yl; 1,4 dihydro-4-oxo-7-methyl-1,8-3-carboxyl-naphthyridin-1-yl; purin-9-yl; pyridin-2-yl; pyrazol-1-yl; or benzimidazol-2-yl.

The most preferred compounds having PAF activity are represented by the following formula VI $$Z^3-X^3-Q^3-W^3 \qquad III$$

and pharmaceutically acceptable acid addition or quaternary salts thereof wherein $Z^3$ is

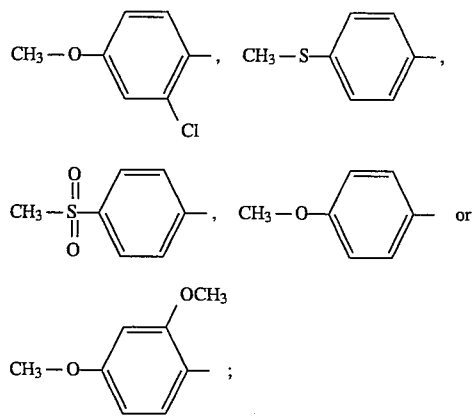

$X^3$ is

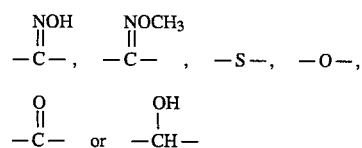

$Q^3$ is lower alkanediyl of 5, 6 or 7 carbon atoms optionally substituted by —OH; tetrahydrofurandiyl; or $(C_1-C_2)$loweralkanediyl-tetrahydrofurandiyl-$(C_1-C_2)$-loweralkanediyl, wherein the tetrahydrofuran ring is substituted with 0–2 hydroxy groups;

$W^3$ is

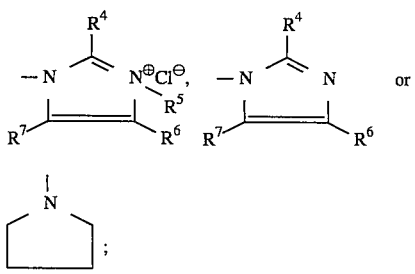

$R^4$ is hydrogen, loweralkyl or hydroxy loweralkyl;
$R^5$ is lower alkyl;
$R^6$ and $R^7$ are independently one or more of hydrogen, loweralkyl, amino loweralkyl or nitro.

The compounds of this invention are conventionally formulated for oral, parenteral, topical and transdermal use, oral is preferred.

This invention includes within its scope pharmaceutical compositions comprising the compounds of this invention in admixture with a pharmaceutically acceptable carrier therefor. In addition, the present invention also includes the use of the compounds of formulas I and II for preparing pharmaceutical compositions useful for treating viral infections or inflammation, or for inhibiting platelet activating factor. In the foregoing compositions, the active compounds of this invention can be used alone as the sole active antiviral agent, sole active antiinflammatory agent or sole active PAF antagonist, or in combination with other therapeutic agents.

For the preferred oral administration, the compounds of this invention are typically formulated in the form of tablets, capsules, elixirs, solutions, suspensions and the like preferably solutions. For parenteral administration, they may be formulated into solutions or suspensions. Topical formulations such as lotions, creams, ointments, sprays and mechanical delivery devices, e.g. transdermal can also be made with the compounds of this invention.

Typical pharmaceutically acceptable carriers for use in the formulations described above are exemplified by: sugars such as lactose, starches such as corn starch, cellulose and derivatives such as sodium carboxymethyl cellulose, ethyl cellulose and methyl cellulose; and other carriers well known in the art. The compositions may also contain preservatives, aerosol propellants and coloring, thickening, suspending, dispensing, emulsifying, wetting, stabilizing and buffering agents.

The dosage of the compounds of this invention which is administered is dependent, in the judgment of the attending clinician, upon a variety of factors, e.g. the age and weight of the individual being treated, the mode of administration, the potency of the administered compound, the indication for which the drug is administered and the severity of the ailment being treated.

Typically, the dosage administered per day for treating viral infections will be oral administration of from about 1 mg/kg to about 75 mg/kg daily in single or divided doses, with about 1–25 mg/kg preferred. The dosage for treating inflammation is about 25 mg to about 2 gm administered daily in divided doses, with the preferred range being about 25 to about 100 mg.

In order to achieve PAF antagonism, oral administration daily in single or divided doses of about 2.5 mg/kg to about 50 mg/kg can be used, preferably about 2.5 mg/kg to about 25 mg/kg. Intravenous administration can be about 0.5 mg/kg to about 10 mg/kg per day with 0.5 mg/kg to about 5 mg/kg preferred.

It is believed that the compounds of this invention are non-toxic when administered in the therapeutic dosages described above.

The compounds of this invention are prepared by the following methods:

(A) to produce a compound of formula I, a compound of the formula

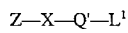
Z—X—Q'—L$^1$ wherein Z and X are as defined previously,

Q' is the same as Q defined previously, or, provided Q in formula I is to contain at least one of the group

wherein each R is independently hydrogen or lower alkyl, Q' may also be the same as Q defined above minus at least one of the groups

and

L$^1$ is a leaving group, with a compound having the formula

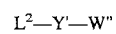
L$^2$—Y'—W"

where L$^2$ is a leaving group,

W" is as defined for W in formula I, or a tautomer thereof, and

Y' is the same Y defined in formula I, or, provided Q in formula I is to contain at least one of the groups

wherein each R is independently hydrogen or lower alkyl, Y' may also be the same as Y defined in formula I plus at least one of the groups

or (B) to produce a compound of formula II and possibly a compound of formula I, at least one compound of the formula

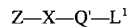
Z—X—Q'—L$^1$ wherein Z, X, Q' and L$^1$ are as defined previously is reacted with a compound of the formula

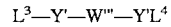
L$^3$—Y'—W'''—Y'L$^4$ wherein L$^3$ and L$^4$ are leaving groups
each Y' is independently as defined above, and
W''' is divalent W' as defined above, or (C) to produce a compound of formula I wherein Z and W are the same and X and Y are the same, reacting a compound of the formula

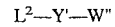
L$^2$—Y'—W"

wherein Y' and W" are as defined previously and
L$^2$ is a leaving group, with a compound of the formula

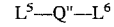
L$^5$—Q"—L$^6$ wherein L$^5$ and L$^6$ are leaving groups and Q" is divalent Q' as defined above, wherein in the above processes, any reactive groups are protected if necessary or desired, the above processes followed, if necessary or desired. by (i) removal of any protecting groups, (ii) conversion of a compound so produced to another compound of formula I or formula II, (iii) if more than one compound of formulas I or II is produced, separation of the compounds so produced, or (iv) conversion of any of the compounds so produced to an acid addition, basic addition, or quaternary amine salt or pharmaceutically acceptable solvate thereof.

In process (A), L$^1$ is preferably bromine or most preferably iodine and L$^2$ is a preferably alkali metal such as sodium, potassium or cesium. The reaction takes place at temperatures of from about −20° C. to 60° C. in an inert organic solvent such as dimethylsulfoxide (DMSO), dimethylformamide (DMF) or tetrahydrofuran (THF). In most cases the final compounds can be converted to water-soluble acid addition or quaternary salts by conventional reactions, e.g., with hydrochloric acid or a quaternizing agent such as methyl sulfonic acid.

The starting compounds Z—X—Q'—L$^1$ wherein L$^1$ is halogen (Hal) are prepared by the following reaction:

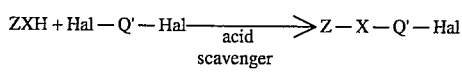

wherein Z, X and Q' are as defined above.

The reaction takes place in the presence of an acid scavenger such as $K_2CO_3$ or organic bases such as collidine and also Hunigs base. The preferred Hal group is iodine although bromine can also be used. The compound Hal—Q'—Hal wherein Hal is iodine can be prepared by reacting Br—Q'—Br with sodium iodide except when Q' is —$CH_2$— or —$CH_2$—$CH_2$—.

Alternatively ZXQ'—I can be prepared by reacting ZXH with Br—Q'—Br to obtain ZXQ'Br, then reacting ZXQ'Br with sodium iodide to obtain Z—X—Q'—I. Or for compounds when Q' is —$CH_2$— or —$C_2H_4$—, Z—X—Q'—I can be prepared by reacting the corresponding mono or dihydric alcohol with HI.

When W is a nitrogen containing heterocyclic moiety, the processes described above result in the W moiety being substituted at a nitrogen atom of the heterocyclic ring, unless the nitrogen atom is protected. In order to make a compound wherein the heterocyclic is substituted at a ring carbon, it is necessary to protect the nitrogen with a group which is easily removed after the C-substitution is carried out and is not removed during the C-substitution reaction, e.g., the trityl group.

Thus, for example, in the preparation of a 2-substituted imidazole, the following reaction scheme is followed:

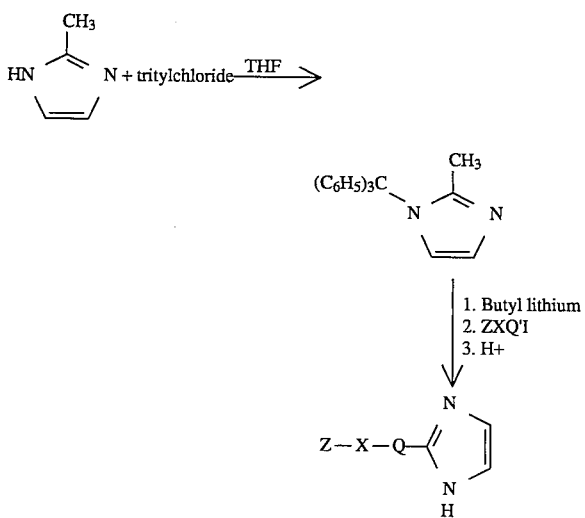

wherein Q, Q', Z and X are as defined above. In this case the methyl group on the imidazo ring becomes part of Q in the compound produced.

In process (B) to make a compound of formula II, the W' moiety should have two ring carbons initially substituted with trimethylsilyloxy groups. When the reaction with Z—X—Q'—I is conducted, the resulting product is a disubstituted W' moiety as shown in the following reaction in which the trimethylsilyloxy substituted compound is illustrated as a pyrimidine.

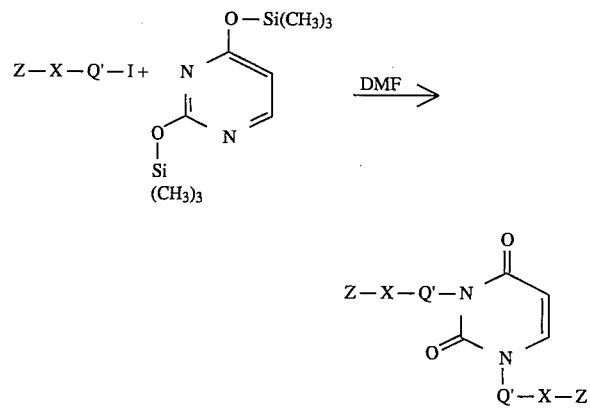

The reaction is carried out at room temperature.

In process (B) if an excess of the compound Z—X—Q'—$L^1$ is used, the product will primarily be of formula II. However, if only small amounts of the compound Z—X—Q'—$L^1$ is used, products of formulas I and II will be produced. The reaction conditions are the same as in process (A).

To produce a compound of formula II wherein at least one of Z, X or Q is not identical with the other Z, X or Q two different compounds having the general formula Z—X—Q'—$L^1$ are used. The result is a mixture of compounds, which may be isolated by standard techniques.

Process C, which produces compounds of formula I wherein Z and W are the same and X and Y are the same, is carried out under the same reaction conditions as process (A).

The preparation of compounds wherein Q is an unsaturated chain, i.e. an alkynediyl or alkenediyl, is illustrated in the following reaction:

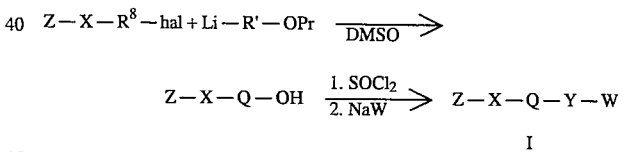

wherein $R^8$ is lower alkyl of 2 to 4 carbons and R' is lower alkynyl of 3 carbons, Y is a bond, Pr is a hydroxy protecting group and hal is bromine or iodine.

The alkenediyl is prepared by partially reducing the alkynediyl compound by catalytic hydrogenation.

The preparation of compounds in which Q is an alkyl having a cycloalkane in the chain is illustrated by the following reaction:

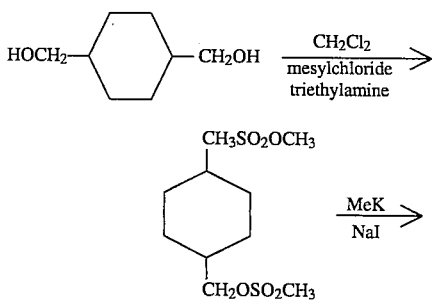

-continued

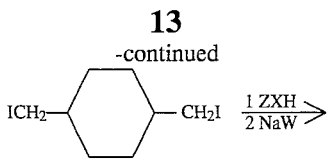

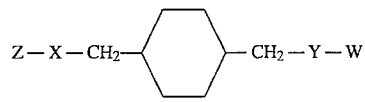

wherein hal is bromine or iodine and Z, X, Y and W are as defined above for formula I.

The preparation of compounds in which Q is a tetrahydrofuran radical having the 2,5-trans stereochemistry is illustrated by the following reaction sequence:

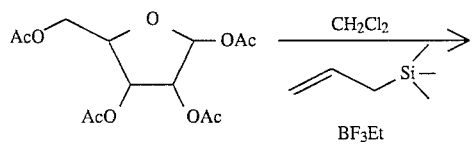

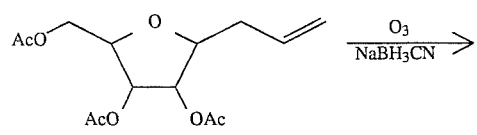

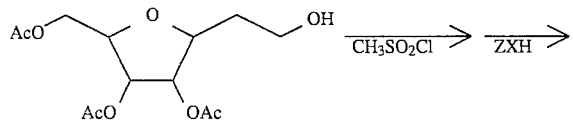

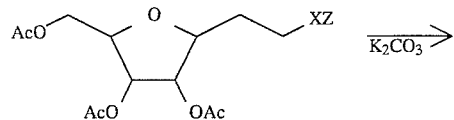

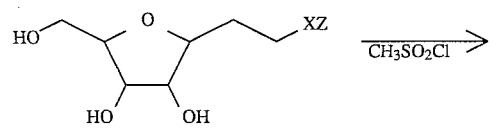

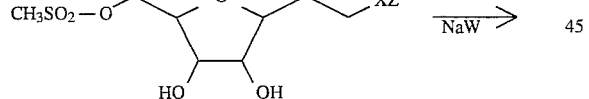

wherein W, X and Z are as defined above.

Alternatively, the following reaction sequence can be used to prepare 2,5-trans tetrahydrofuran compounds:

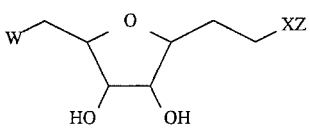

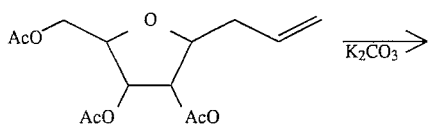

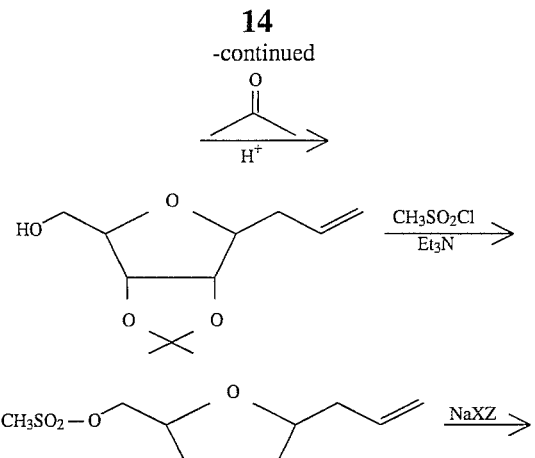

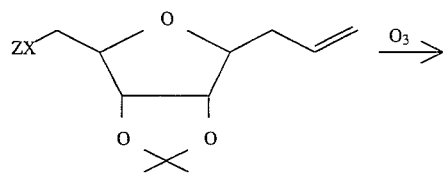

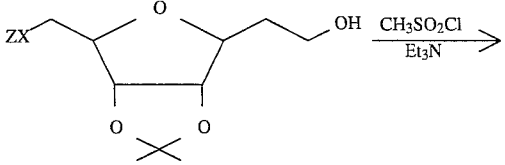

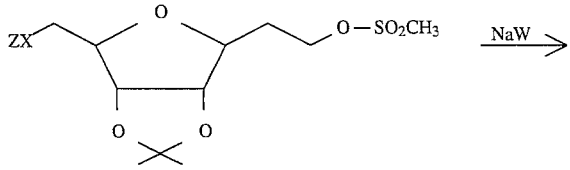

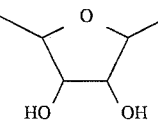

wherein X, Z and W are as defined above.

For compounds wherein Q is a tetrahydrofuran radical having the 2,5-cis stereochemistry, the following reaction sequence is exemplary:

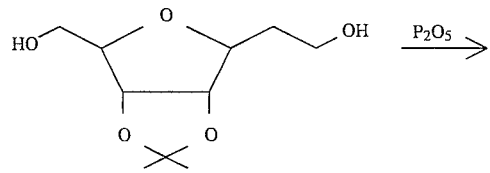

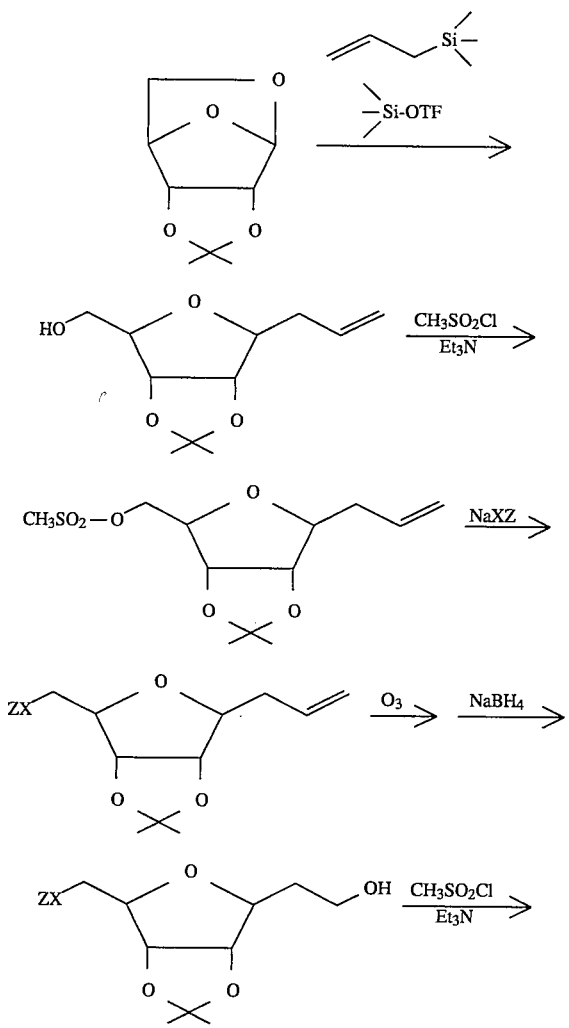

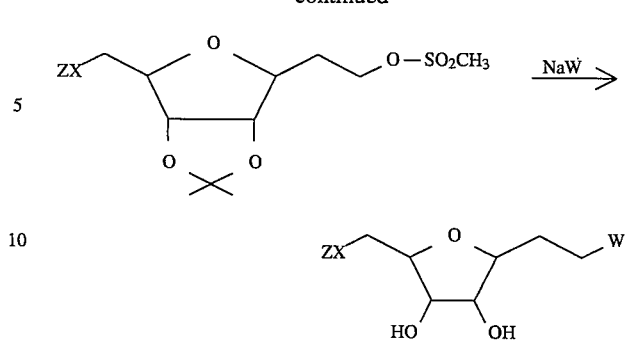

A compound of formula I or II can be converted to a different compound of formula I or II, respectively, by standard techniques well known in the art. Such conversion techniques are illustrated in the examples.

In general preparing the compounds of this invention involves relatively simple procedures as illustrated by the many examples which appear later in this text.

The following Table I shows the compounds of formula I prepared by the processes described above.

TABLE I

| Example | Z | X | Q | Y | W | Salt |
|---|---|---|---|---|---|---|
| 1. | CH₃O-phenyl-Cl | —O— | —(CH₂)₆— | bond | N-methylimidazole | HCl |
| 2. | " | " | " | —S— | thiazolidinone | — |
| 3. | " | " | " | " | N-CH₃ tetrazole | — |
| 4. | " | " | " | —S— | HO-pyridine | — |

TABLE I-continued

| Example | Z | X | Q | Y | W | Salt |
|---|---|---|---|---|---|---|
| 5. | " | " | " | bond | 1-methyltetrazole (N1-linked) | — |
| 5A. | " | " | " | " | 2-methyltetrazole (N2-linked) | — |
| 6. | 4-methoxy-2-chlorophenyl (CH₃O-, Cl-substituted phenyl) | —O— | —(CH₂)₆— | bond | 1-methylimidazole | — |
| 7. | " | " | " | " | 1-methyl-5-amino-tetrazole | — |
| 7A. | | " | " | —NH— | 5-methyltetrazol-2-yl (NH) | — |
| 9. | " | " | " | bond | 1-methyluracil | — |
| 10. | " | " | " | " | 4-hydroxymethyl-1-methylimidazole | HCl |
| 10A. | " | " | " | " | 5-hydroxymethyl-1-methylimidazole | " |
| 11. | " | " | " | " | 1,2-dimethylimidazole | " |
| 12. | 4-methoxy-2-chlorophenyl | —O— | —(CH₂)₆— | bond | 1-methyl-5-nitroimidazole | — |
| 13. | " | " | —(CH₂)₇— | " | pyridine | HCl |
| 14. | 4-(1,3-dioxolan-2-yl)phenyl | " | —(CH₂)₆— | " | 1-methylimidazole | " |

TABLE I-continued

| Example | Z | X | Q | Y | W | Salt |
|---|---|---|---|---|---|---|
| 15. | 4-methoxy-2-chlorophenyl | " | —(CH₂)₇— | " | " | " |
| 16. | " | " | —(CH₂)₅— | " | " | " |
| 17. | " | " | —(CH₂)₁₀— | " | " | " |
| 18. | 3-methyl-5-isoxazolyl | bond | —(CH₂)₇— | " | " | " |
| 19. | 4-methoxy-2-chlorophenyl | —O— | —(CH₂)₆— | " | 1-methylbenzimidazol-2-yl | HCl |
| 20. | " | " | " | " | 1-methyl-2-hydroxybenzimidazolyl | — |
| 21. | " | " | " | " | 4-(hydroxymethyl)-1-methylimidazol-5-yl | HCl |
| 21A. | " | " | " | " | 5-(hydroxymethyl)-1-methylimidazol-4-yl | " |
| 22. | " | " | " | " | 1-methylpyrrolidinyl | " |
| 23. | 1-methylimidazol-2-yl | bond | " | " | imidazol-1-yl | " |
| 24. | 4-methoxy-2-chlorophenyl | —O— | " | " | 7-methyl-4-oxo-1,8-naphthyridine-3-carboxylate sodium | — |

TABLE I-continued

| Example | Z | X | Q | Y | W | Salt |
|---|---|---|---|---|---|---|
| 25. | 1-methyl-2-methylimidazole | bond | —(CH₂)₆— | bond | 2-methylimidazol-1-yl | HCl |
| 26. | 3-chloro-4-methoxyphenyl | —O— | " | " | 2-methyl-1-methylpyrazol-5-yl | — |
| 27. | " | " | " | " | purin-9-yl | — |
| 27A. | " | " | " | " | purin-7-yl isomer | — |
| 28A. | " | " | " | " | (4-methyl-5-hydroxymethyl)imidazol-1-yl | HCl |
| 28. | " | " | " | " | (4-methyl-5-hydroxymethyl)imidazol-1-yl | " |
| 29. | " | " | " | " | 2-ethylimidazol-1-yl | " |
| 30. | 3-chloro-4-methoxyphenyl | —O— | —(CH₂)₆— | —S— | benzimidazol-2-yl | — |
| 31. | " | " | " | bond | 2-ethyl-5-methylimidazol-1-yl | HCl |

TABLE I-continued

| Example | Z | X | Q | Y | W | Salt |
|---|---|---|---|---|---|---|
| 31A. | " | " | " | " | 2-ethyl-1-methyl-5-methyl-imidazole | " |
| 32. | " | " | —(CH₂)₃— | " | 1-methylimidazole | " |
| 33. | " | " | —(CH₂)₇— | " | 1,2-dimethylimidazole (N-methyl) | " |
| 34. | " | " | " | " | 2-methylimidazole | " |
| 35. | " | " | " | " | 1-butyl-2-methylimidazole | " |
| 36. | 4-phenoxyphenyl | —O— | —(CH₂)₆— | bond | 1-methylimidazole | HCl |
| 37. | 3-chloro-4-methoxyphenyl | " | " | " | 4,5-bis(methoxycarbonyl)-1-methylimidazole | — |
| 38. | " | " | " | " | 4,5-bis(hydroxymethyl)-1-methylimidazole | HCl |
| 39. | " | " | trans-cyclohexyl | " | imidazole (N-) | " |
| 40. | tert-butyl (H₃C—C(CH₃)₂—) | bond | —CC—(CH₂)₆— | " | " | " |
| 41. | 3-chloro-4-methoxyphenyl | —O— | —(CH₂)₆— | " | 1,3-dimethylimidazolium | I⁻ |

5,459,144

TABLE I-continued

| Example | Z | X | Q | Y | W | Salt |
|---|---|---|---|---|---|---|
| 42. | " | " | " | " | (N-methyl pyrazole with CH₂NH₂) | HCl |
| 42.A | 4-methoxy-2-chlorophenyl | —O— | —(CH₂)₆— | bond | (N-methyl pyrazole with CH₂NH₂) | HCl |
| 43. | " | " | " | " | (N-methyl pyrazole with two CH₃ groups) | " |
| 44. | " | " | " | " | (N-methyl imidazole with CH₂OH) | " |
| 45 | " | " | —(CH₂)₇— | " | (2-methyl imidazole N-CH₂C(O)OCH₂CH=CH₂) | " |
| 46. | " | " | " | " | (2-methyl imidazolium N-CH₂COO⁻) | — |
| 47. | " | " | —(CH₂)₃—C≡C—CH₂— | " | —N⟨imidazole⟩N | HCl |
| 48. | " | " | —(CH₂)₇— | " | (2-methyl imidazole N-CH₂CH₂NH₂) | " |
| 49. | 4-methoxy-2-chlorophenyl | —O— | —(CH₂)₇— | bond | (2-methyl imidazole N-CH₂CH₂OH) | HCl |
| 50. | phenyl | bond | —CC(CH₂)₆— | bond | (N-methyl imidazole) | " |

5,459,144

TABLE I-continued

| Example | Z | X | Q | Y | W | Salt |
|---|---|---|---|---|---|---|
| 51. | 2-chloro-4-methylphenyl | -CH(OH)- | -(CH₂)₅- | bond | imidazol-1-yl | " |
| 52. | 4-methoxyphenyl | -C(=O)- | -(CH₂)₆- | bond | " | " |
| 53. | " | -CH(OH)- | " | " | " | " |
| 54. | " | bond | -CH=CH(CH₂)₅- | " | " | " |
| 55. | 4-methoxyphenyl (CH₃O–) | -C(=NOH)- | -(CH₂)₆- | " | 1-methylimidazol-... | HCl |
| 56. | " | bond | -(CH₂)₇- | " | " | " |
| 57. | 4-(methylthio)phenyl | -C(=O)- | -(CH₂)₆- | " | " | " |
| 58. | " | -C(=NOH)- | " | " | " | " |
| 59. | " | -CH(OH)- | " | " | " | — |
| 60. | 4-(methylsulfonyl)phenyl | -C(=O)- | " | " | " | HCl |
| 61. | 4-(methylsulfonyl)phenyl | -C(=NOCH₃)- | -(CH₂)₇- | bond | imidazol-1-yl | HCl |
| 62. | " | -C(=NOH)- | " | " | " | " |
| 63. | " | -C(=O)- | " | " | " | " |
| 64. | adamantyl | -NH-C(=O)- | -(CH₂)₅- | " | " | " |
| 65. | 3-chloro-5-methyl-2-methoxyphenyl | bond | -(CH₂)₆- | " | " | " |

TABLE I-continued

| Example | Z | X | Q | Y | W | Salt |
|---|---|---|---|---|---|---|
| 65A. | 4-Cl, 3-CH₃, 2-OCH₃ phenyl (Cl, CH₃, OCH₃ substituted phenyl) | " | " | " | " | " |
| 66. | 4-methoxyphenyl (H₃C-O-C₆H₄-) | $-\overset{O}{\underset{\|}{C}}-$ | —(CH₂)₅— | bond | 1-methylimidazole | HCl |
| 67. | 2,4-dimethoxyphenyl | $-\overset{O}{\underset{\|}{C}}-$ | " | bond | " | " |
| 68. | " | $-\underset{H}{\overset{OH}{\underset{\|}{C}}}-$ | " | " | " | — |
| 69. | " | bond | —CH=CH(CH₂)₄— | " | " | HCl |
| 70. | 4-methoxy-2-chlorophenyl | $-\overset{O}{\underset{\|}{C}}-$ | —(CH₂)₅— | " | " | " |
| 71. | 4-methoxyphenyl | $-\underset{H}{\overset{OH}{\underset{\|}{C}}}-$ | " | " | " | — |
| 72. | 4-methoxyphenyl | bond | —CH=CH(CH₂)₄— | bond | 1-methylimidazole | HCl |
| 73. | 4-methoxy-2-chlorophenyl | $-\underset{H}{\overset{OH}{\underset{\|}{C}}}-$ | —(CH₂)₅— | " | " | — |
| 74. | 4-methoxyphenyl | bond | —(CH₂)₆— | " | " | HCl |
| 75. | 2-naphthyl | —O— | —(CH₂)₆— | " | " | " |
| 76. | 4-(methylthio)phenyl | —O— | —(CH₂)₆— | " | " | " |

5,459,144

TABLE I-continued

| Example | Z | X | Q | Y | W | Salt |
|---------|---|---|---|---|---|------|
| 77. | 4-(H₃C-SO₂-)phenyl- | " | " | " | " | " |
| 78. | 4-(CH₃O-)phenyl- | —S— | —(CH₂)₆— | bond | 1-methylimidazol-2-yl (N-CH=N ring, N-methyl) | HCl |
| 79. | " | —SO₂— | " | " | " | " |
| 26A. | " | —O— | " | " | 3-methylpyrazol-1-yl | " |
| 80. | 4-(CH₃O-)phenyl- | —C(=O)— | —CH(CH₃)(CH₂)₆— | " | imidazol-1-yl | " |
| 81. | 3-Cl-4-CH₃-phenyl- | —NHC(=O)— | —(CH₂)₅— | " | " | " |
| 82. | " | —N(CH₃)— | —(CH₂)₆— | " | " | " |
| 83. | " | —N(CH₃)C(=O)— | —(CH₂)₅— | " | " | " |
| 84. | " | —NH— | —(CH₂)₆— | " | " | " |
| 85. | 3,5-di(CH₃O-)phenyl- | —CH₂O— | " | " | " | " |
| 86. | 3-Cl-4-CH₃O-phenyl- | —O— | tetrahydrofuran-2,5-diyl with 3,4-diOH (propyl/ethyl substituents) | " | " | " |
| 87. | " | " | " | " | 1,2,4-triazol-1-yl | " |
| 88. | 3-Cl-4-CH₃O-phenyl- | —O— | tetrahydrofuran-2,5-diyl with 3,4-diOH | bond | imidazol-1-yl | HCl |
| 89. | " | " | 2,5-dihydrofuran-2,5-diyl (with propyl/ethyl substituents) | " | " | " |

TABLE I-continued
| Example | Z | X | Q | Y | W | Salt |
|---|---|---|---|---|---|---|
| 90. | " | " | 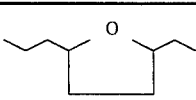 | " | 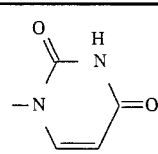 | — |
| 91. | " | " | 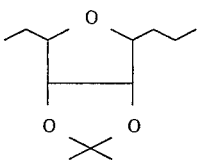 | " | " | — |
| 92. | " | " | 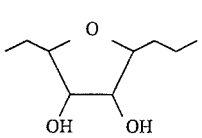 | " | " | " |
| 93 and 97. | " | " | " | " | 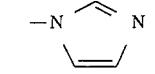 | HCl |
| 94. | " | " | " | —O— | 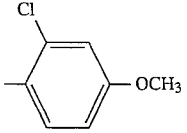 | — |
| 95. | " | " | " | " | 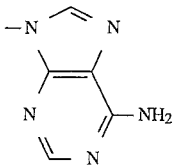 | — |
| 96 and 98. | " | " | " | bond | 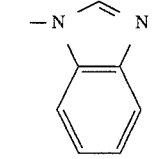 | HCl |
| 99. | " | " | " | 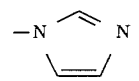 | — | |
| 100. | " | " | " | " | HCl | |
| 101. | " | " | " | " | " | |
| 102. | —O— | —(CH$_2$)$_6$— | bond | 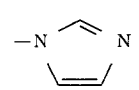 | HCl | |
| 103. | " | " | " | " | " | |
| 104. | " | " | " | " | " | |
| 105a. | 2,4-dichlorophenyl | " | " | " | " | " |
| 105b. | 4-chloro-3-methylphenyl | " | " | " | " | " |
| 105c. | 2-chloro-5-methylphenyl | " | " | " | " | " |
| 105d. | 2-chloro-4,5-dimethylphenyl | " | " | " | " | " |
| 105e. | 3,5-dimethyl-4-chlorophenyl | " | " | " | " | " |

TABLE I-continued

| Example | Z | X | Q | Y | W | Salt |
|---|---|---|---|---|---|---|
| 105f. | 2,4-difluorophenyl | " | " | " | " | " |
| 105g. | 2-methyl-4-chlorophenyl | " | " | " | " | " |
| 105h. | 2,6-dimethyl-4-chlorophenyl | " | " | " | " | " |
| 105i. | 2-chloro-6-methylphenyl | " | " | " | " | " |
| 105j. | 2-bromo-4-methylphenyl | —O— | —(CH$_2$)$_6$— | bond | imidazolyl (—N⟨N⟩) | HCl |
| 105k. | 2,6-dichlorophenyl | " | " | " | " | " |
| 106. | " | " | " | " | " | " |

The following Table II shows the components of the compounds of Formula II.

examples which follow by substituting the appropriate starting materials for those in the examples.

TABLE II

| Example | Z | X | Q | Y | W' | Y | Q | X | Z |
|---|---|---|---|---|---|---|---|---|---|
| 8. | 4-methoxy-2-methyl-chlorophenyl (CH$_3$O-, Cl-substituted phenyl) | —O— | —(CH$_2$)$_6$— | bond | N-methyl maleimide-type ring | bond | —(CH$_2$)$_6$— | —O— | 4-methoxy-2-methyl-chlorophenyl |
| 20. | " | " | " | " | N,N'-dimethyl benzimidazolone | " | " | " | " |

The following Table III shows additional compounds which can be prepared by following the procedures of the

TABLE III

| Z | X | Q | Y | W | Salt |
|---|---|---|---|---|---|
| phenyl | bond | —(CH$_2$)$_6$—C≡C— | bond | imidazolyl (—N⟨N⟩) | HCl |
| 4-methoxyphenyl (CH$_3$O-phenyl) | " | —(CH$_2$)$_6$—CH=CH— | " | " | HCl |
| " | —O— | —CH$_2$-(phenyl)-CH$_2$— | " | " | " |

TABLE III-continued

| Z | X | Q | Y | W | Salt |
|---|---|---|---|---|------|
| " | " | (tetrahydrofuran-2,4-diyl-bis(methylene) structure with ethyl substituent) | " | " | " |
| " | " | $-CH_2-$(tetrahydropyran-2,5-diyl)$-CH_2-$ | " | " | " |

The starting materials for use in the preparation of the compounds of this invention are either commercially available or are prepared by conventional means known in the art.

The following examples illustrate the invention. Fast atom bombardment (FAB) mass spectra (MS) were run on a Finnigan MAT 312 double focussing mass spectrometer, operating at an accelerating voltage of 3 kV. The MS samples were ionized by bombardment with xenon atoms produced by a saddle field ion source from Ion Tech operating with a tube current of 2 mA at an energy of 6 KeV. The MS results are reported as the free base plus a proton. The proton nuclear magnetic resonance ($H^1$-NMR) spectra were recorded at 200 MHz on a Varian XL-200 spectronometer; all chemical shift values δ are reported in ppm downfield from tetramethylsilane.

EXAMPLE 1

1-[6-(2-chloro-4-methoxyphenoxy)hexyl]imidazole

Add 200 mg. 6-(2-chloro-4-methoxyphenoxy)hexyl-1-bromide in 1.5 ml of dimethyl formamide (DMF) to 180 mg sodium imidazole in a reaction vial at room temperature, stir 2 hours then add 20 mg sodium iodide, stir overnight. Add methylene chloride, wash with water then brine, elute on a coarse silica column with methylene chloride then a mixture of 50% ethylacetate and methylene chloride (v/v) to isolate the title compound.

EXAMPLE 2

2-{[6-(2-chloro-4-methoxyphenoxy)hexyl]thio}-4,5-dihydrothiazol-4-one (a) Reflux about 500 mg sodium iodide in 10 ml of acetone with 350 mg. 6-(2-chloro-4-methoxyphenoxy)hexyl-1-bromide for 5 to 10 minutes, remove the acetone by bubbling nitrogen through the reaction mixture, add methylene chloride, wash with water, then brine and dry over sodium sulfate to obtain 6-(2-chloro-4-methoxyphenoxy)hexyl-1-iodide.

(b) Add 3 grams of 6-(2-chloro-4-methoxyphenoxy)hexyl-1-iodide in 10 ml acetonitrile to 1.2 g rhodanine and 20 g cesium carbonate. Stir overnight, then remove the acetonitrile, add methylene chloride and wash with water then brine and dry over sodium sulfate. Elute on a coarse silica column with methylene chloride followed by 5% ethylacetate/methylene chloride and finally 10% ethylacetate/methylene chloride to yield the title compound isolation.

EXAMPLE 3

5-{[6-(2-chloro-4-methoxyphenoxy)hexyl]thio}-1-methyltetrazole

Reflux 350 mg. 6-(2-chloro-4-methoxyphenoxy) hexyl-1-bromide with 10 ml of acetone and about 500 mg. sodium iodide for five to ten minutes, remove the acetone by bubbling nitrogen through the reaction mixture, add methylene chloride, wash with water, then brine and dry over sodium sulfate to obtain 6-(2-chloro-4-methoxyphenoxy)hexyl-1-iodide. Add 133 mg of 5-mercapto-1methyltetrazole, 268 mg. cesium carbonate and 3 ml acetonitrile to the iodide product, stir overnight, add methylene chloride and wash with water, sodium carbonate, water, then brine and dry over sodium sulfate. Remove the solvent and recover the title compound as crystals.

EXAMPLE 4

2-{[6-(2-chloro-4-methoxyphenoxy)hexyl]-thio}-3-pyridinol

Stir 300 mg. of the iodide prepared in Examples 2 or 3, 3 ml. acetonitrile 112 mg. 2-mercapto-3-pyridinol and 201 mg. cesium carbonate in a reaction flask overnight at room temperature. Remove the acetonitrile and add methylene chloride. Wash with sodium carbonate solution, water, then brine and dry over sodium sulfate. Remove the solvent then add methylene chloride, heat to dissolve the mixture, add hexane and cool to precipitate the title compound as white crystals.

EXAMPLE 5

1 and
2-[6-(2-chloro-4-methoxyphenoxy)hexyl]tetrazole

Stir overnight at room temperature 300 mg. of the iodide prepared in Examples 2 and 3, 3 ml. acetonitrile, 63 mg. 1-H-tetrazole and 274 mg. cesium carbonate in a reaction flask. Add an additional. 189 mg. 1-H-tetrazole and 100 mg. cesium carbonate, let stir one week at room temperature. Work up the reaction mixture in methylene chloride with a water wash. Elute on a coarse silica column with methylene chloride then ethyl acetate/methylene chloride. Isolate two fractions of the title compound, the less polar fraction and the more polar fraction. One of the fractions is the 1-substituted tetrazole and the other fraction is the 2-substituted tetrazole.

EXAMPLE 6

1-[6-(2-chloro-4-methoxyphenoxy)hexyl]-1,2,4-triazole

Stir overnight at room temperature, 300 mg. of the iodide prepared in Examples 2 or 3, 3 ml. acetonitrile, 225 mg. 1,2,4-triazole and 274 mg. cesium carbonate in a reaction flask. Work up the reaction mixture in methylene chloride with a water wash and elute on a silica column with methylene chloride and ethylacetate to recover the title compound.

EXAMPLE 7

1 or 2-[6-(2-chloro-4-methyoxyphenoxy)hexyl]-5-amino-tetrazole and
5-{[6-(2-chloro-4-methoxyphenoxy)hexyl]-amino}-tetrazole Stir overnight at room temperature, 300 mg. of the iodide prepared in Examples 2 or 3, 2 ml. dimethyl formamide DMF, 421 mg. 5-amino tetrazole and 274 mg. cesium carbonate. Test the product on thin layer chromatography (TLC) with 50% ethyl acetate/hexanes. The test indicates that two separate compounds resulted, one more polar than the other. Separate the less polar title compound and the more polar title compound on a coarse silica column by eluting with methylene chloride followed by 5% ethyl acetate/methylene chloride, then 10% ethyl acetate/methylene chloride. The more polar compound is highly crystalline. The less polar of the compounds is the 1 or 2 substituted tetrazole, and the more polar is the exocyclic nitrogen substituted tetrazole title compound.

EXAMPLE 8

1,3-di-[6-(2-chloro-4-methoxyphenoxy)hexyl]-1,2,3,4-tetrahydropyrimidine-2,4-dione Stir overnight at room temperature, 300 mg. of the iodide prepared in Examples 2 or 3, 1.83 gm. 2,4 di-trimethylsilyloxypyrimidine, anhydrous DMF and 1.24 gm. cesium fluoride in a reaction flask. Work up with a water wash in methylene chloride, elute on a coarse silica gel column with methylene chloride followed by 10% ethyl acetate/methylene chloride then 20% ethyl acetate/methylene chloride to isolate the title compound.

EXAMPLE 9

1-[6-(2-chloro-4-methoxyphenoxy)hexyl]-1,2,3,4-tetrahydropyrimidine-2,4-dione

Stir overnight at room temperature, 300 mg. of the iodide made in Examples 2 or 3, 1 ml. acetonitrile, 274 mg. cesium carbonate, 270 mg. of 2N-benzoyl uracil, 1 ml. of DMF (to enhance solubility) and 100 mg. additional of cesium carbonate in a reaction flask. Work up in methylene chloride with water and add methanolic potassium carbonate then again stir overnight at room temperature. Work up in methylene chloride with a water wash. Elute on a coarse silica column with methylene chloride and sequently 10%, 20%, 30% and 40% ethyl acetate/methylene chloride to obtain the title compound as an oil which crystallizes upon standing.

EXAMPLE 10

1-[6-(2-chloro-4-methoxyphenoxy)hexyl]-4-and 5-hydroxymethylimidazole

Add 200 mg. of the iodide made in Examples 2 or 3 to 20 ml. DMF, then add 500 mg. NaOH and finally 200 mg. 4-hydroxymethyl imidazole to a reaction flask, stir at room temperature for about 24 hours.

Add methylene chloride and wash with water, then brine and dry over sodium sulfate. Elute on a coarse silica column with methylene chloride, then 5% methanol/methylene chloride, then 10% methanol/methylene chloride and isolate a mixture of the title compounds. The isomers are separated on TLC with ethylacetate, and finally on a coarse silica column with 50% ethylacetate/THF to yield the title compounds as the less polar isomer in fractions 5–8 and the more polar isomer in fractions 11–18. Prepare the hydrochloride salts by reaction with 0.1N HCl.

EXAMPLE 11

1-[6-(2-chloro-4-methoxyphenoxy)hexyl]-2-methylimidazole

Stir about 5 hours at room temperature, 200 mg. of the iodide made in Examples 2 or 3, 134 mg. 2-methylimidazole, 3 ml. DMF and 69 mg. sodium hydroxide in a reaction flask. Work up in methylene chloride with a water wash, then brine, then dry over sodium sulfate to recover the title compound as an oil which crystallizes on standing. Prepare the hydrochloride salt by reaction with 0.1N HCl.

EXAMPLE 12

1-[6-(2-chloro-4-methoxyphenoxy)hexyl]-4-nitroimidazole

Stir overnight at room temperature, 200 mg. of the iodide made in Examples 2 or 3, 3 ml. DMF, 184 mg. 4-nitroimidazole and 69 mg. sodium hydroxide in a reaction flask. Work up with methylene chloride and a water wash. Elute on a coarse silica column with methylene chloride then ethylacetate to obtain the title compound.

EXAMPLE 13

2-[7-(2-chloro-4-methoxyphenoxy)heptyl]pyridine

Under a nitrogen atmosphere, add 152 mg. 2-picoline and 1.5 ml. tetrahydrofuran (THF) and cool to −28° C. Add 104 mg. n-butyl lithium and stir about 30 minutes at −78° C. Add 20 mg. of the iodide prepared in Examples 2 and 3 in 1 ml. THF. Stir 1 hour at −78° C., let warm to room temperature and stir about 15 hours. Work up with water and methylene chloride then wash with water and brine then dry over sodium sulfate. Elute on a coarse silica column with methylene chloride then 50% ethylacetate/methylene chloride to obtain the title compound. Prepare the hydrochloride salt by reaction of the title compound with 0.1N HCl.

EXAMPLE 14

1-{6-[4-(4,5-dihydro-2-oxazolyl)phenoxy]hexyl}imidazole (a) Prepare 6-[4-(4,5-dihydro-2-oxazolyl)phenoxy]-hexyl-1-iodide by adding 10 gm. of 4-(4,5-dihydro-2-oxazolyl)phenol, 24.4 gms.. 1,6-dibromohexane, 10 gm. sodium iodide, 35 gm potassium carbonate and 250 ml. acetonitrile in a reaction flask. Purge with nitrogen, reflux for 24 hours, cool and filter off resulting solid. Remove acetonitrile and extract with ethylacetate. Remove the ethylacetate to yield an oil/solid. Purify on silica with methylene chloride to recover the product.

(b) Add 200 mg. of the product from part (a), 300 mg. of sodium imidazole and 10 ml. of dimethylformamide (DMF) to a flask and stir for 48 hours. Partition the reaction mixture water/methylene chloride. Elute on a silica column with 100% ethylacetate followed by 10% methanol/methylene chloride to yield the title compound.

Prepare the hydrochloride salt by adding 6 ml. of 0.1N HCl.

MS: m/z 314 (M$^+$)

EXAMPLE 15

1-[7-(2-chloro-4-methoxyphenoxy)heptyl]imidazole (a) Prepare 7-(2-chloro-4-methoxyphenoxy)heptyl-1-iodide by adding 3 gms. of 2-chloro-4-methoxyphenol, 9.8 gms. 1,7-dibromo heptane, and 5.2 gms. potassium carbonate to 75 ml. acetone in a reaction flask. Purge with nitrogen, reflux for 48 hours, cool. Add $CH_2Cl_2$ and wash with water, then brine and dry over sodium sulfate. Elute on a coarse silica column with hexane, 10, 15 and 20% $CH_2Cl_2$/hexane. Isolate product, add 50 ml. acetone, 8.5 g sodium iodide and heat to reflux 10–15 min. Remove acetone, add $CH_2Cl_2$ and wash with water, then brine and dry over sodium sulfate. Remove solvent and recover the product.

(b) Add 2 gms. of the product of step (a), 1.4 gms. sodium imidazole and DMF in a reaction flask, stir for about 24 hours. Work up with methylene chloride and a water wash, remove the solvent under a high vacuum and recover the title compound. Convert the title compound to the hydrochloride salt by reaction with 0.1N hydrochloric acid.

EXAMPLE 16

1-[5-(2-chloro-4-methoxyphenoxy)pentyl]imidazole (a) Prepare 5-[2-chloro-4-methoxyphenoxy)pentyl-1-iodide by mixing 3 gms. 2-chloro-4-methoxyphenol, 8.7 gms. 1,5-dibromo pentane, and 5.2 gms. potassium carbonate to 75 ml. acetone in a reaction flask. Purge with nitrogen, reflux for 48 hours. Add $CH_2Cl_2$ and wash with water, then brine and dry over sodium sulfate. Elute on a coarse silica column with hexane, 10, 15 and 20% $CH_2Cl_2$/hexane. Isolate product, add 50 ml. acetone, 8.5 g sodium iodide and heat to reflux 10–15 min. Remove acetone, add $CH_2Cl_2$ and wash with water, then brine and dry over sodium sulfate. Remove solvent and recover the product.

(b) Add 350 mg. of the product of step (a) to 2 ml. DMF (dimethylformamide) and 300 mg. sodium imidazole in a reaction flask. Stir for about 24 hours. Recover the title compound by treating with methylene chloride, a water wash and brine. Dry over sodium sulfate and remove the solvent to obtain a crystalline compound.

Prepare the hydrochloride salt by reacting 275 mg. of the title compound with 10.2 ml. of 0.1N HCl.

EXAMPLE 17

1-[10-(2-chloro-4-methoxyphenoxy)decyl]imidazole (a) Prepare 10-(2-chloro-4-methoxyphenoxy)decyl-1-iodide by adding 3 g of 2-chloro-4-methoxyphenol, 11.3 g of 1,10-dibromodecane, 75 ml acetone and 5.2 g potassium carbonate in a reaction flask. Reflux for 48 hours, cool and remove acetone. Add $CH_2Cl_2$, wash with water then brine and dry over sodium sulfate. Elute on a coarse silica column with hexane then 15 and 20% $CH_2Cl$/hexane to obtain the product. Take 3.6 g of 10-(2-chloro-4-methoxyphenoxy)decyl-1-bromide, 50 ml acetone and 7.1 g NaI and heat to reflux for 20 mins. Remove acetone, add methylene chloride and wash with water, then brine and dry over sodium sulfate. Remove methylene chloride and recover 10-(2-chloro-4-methoxyphenoxy)decyl1-iodide.

(b) Stir 0.5 gm. of the compound prepared in step (a), 10 ml. DMF and 160 mg. sodium imidazole in a reaction flask for about 24 hours at room temperature. Recover the resulting title compound by treating with methylene chloride, washing with water, then brine, drying over sodium sulfate and removing the solvent. The recovered title compound is crystalline.

Prepare the hydrochloride salt of the title compound by reacting 340 mg. with 33 mg. 0.1N HCl.

EXAMPLE 18

5-[7-(1-imidazolyl)-heptyl]-3-methylisoxazole (a) Prepare 7-(3-methylisoxazole-5-yl)heptyl-1-bromide by adding 20 ml. of 3,5-dimethylisoxazole to 200 ml. THF (tetrahydrofuran) under nitrogen and cool to about −78° C. Slowly add (over 10 minutes) 80 ml. of N-butyl lithium, 2.5M/hexane and stir for 30 minutes. Add the resulting solution to a solution of 244 gm. 1,6-dibromohexane in 100 ml. THF at −78° C. Purge with nitrogen, stir in a dry ice/acetone bath and then allow to warm to room temperature over a period of about 3 hours. Recover the product from the solvent and unreacted starting materials by distillation under reduced pressure (½ mm Hg) b.p. 134°–136° C.

(b) Stir 260 mg. of the compound made in step (a) with 450 mg. sodium imidazole in 2 gms. DMF for one week at room temperature. Partition with water/methylene chloride, elute on a silica column with 100% methylene chloride followed by 100% ethylacetate to yield the title compound. Prepare the hydrochloride salt of the title compound by reaction with 0.1N HCl.

FAB-MS: m/z 248 (M$^+$)—base, HCl salt, H$^1$-NMR-200 mHz; $^\delta$H (CDCl$_3$) 1.37 (6H,s), 1.55–1.80 (2H,m), 1.80–2.00 (2H,m) 2.25 (3H,s), 2.70 (2H,t,J 8Hz), 4.35 (2H,t,J 8Hz), 5.85 (1H,s), 7.18 (1H,s), 7.40 (1H,s), 9.65 (1H,s).

EXAMPLE 19

1-[6-(2-chloro-4-methoxyphenoxy)hexyl]benzimidazole

Stir overnight at room temperature, 300 mg. of the iodide made in Examples 2 or 3, 3 ml. DMF, 145 mg. benzimidazole and 49 mg. sodium hydroxide. Treat with methylene chloride, wash with water, then brine and recover the title compound by removing the solvent.

The hydrochloride salt is made by reacting the title compound with about 1.1 eq. 0.1N HCl.

EXAMPLE 20

1-[6-(2-chloro-4-methoxyphenoxy)hexyl]-2-hydroxybenzimidazole and N,N'-bis-[6-(2-chloro-4-methoxyphenoxy)hexyl]-2-benzimidazolone Stir overnight at room temperature, 1 gm. 2 hydroxybenzimidazole, 2 gms. of the iodide prepared in Examples 2 or 3, 0.35 gm sodium hydroxide and 10 ml DMF in a reaction flask. Partition with water/methylene chloride. Elute on a silica column with 100% methylene chloride, then 50/50 methylene chloride/ethylacetate. Two major fractions are obtained, NMR shows the top spot fraction to be N,N'-bis'-[6-(2-chloro-4-methoxyphenoxy)hexyl]-2-benzimidazolone, FAB-MS: m/z 615 ($M^+$) free base, $H^1$-NMR-200 mHz; $^\delta H$ ($CDCl_3$), 1.35–1.65 (8H,m), 1.70–1.90 (8H,m), 3.75 (6H,s), 3.80–4.05 (8H,m), 6.7–7.2 (10H,m), and the bottom spot fraction to be 1-[6-(2-chloro-4-methoxyphenoxy)hexyl]-2-hydroxybenzimidazole. FAB-MS: m/z 375 ($M^+$); Free Base, $H^1$-NMR-200 mHz; $^\delta H$ ($CDCl_3$), 1.4–1.70 (4H,m), 1.7–1.9 (4H,m), 3.75 (3H,s), 3.85–4.05 (4H,m), 6.7–7.2 (7H,m).

EXAMPLE 21

1-[6-(2-chloro-4-methoxyphenoxy)hexyl]-4- and-5-hydroxymethylimidazole

Stir overnight at room temperature, 3 gm. of the iodide prepared in Examples 2 or 3, 15 ml. DMF, 1.01 gm. sodium hydroxide and 1.64 gm. 4-hydroxymethyl imidazole HCl. Add methylene chloride and wash several times with water. Elute on a coarse silica column with methylene chloride, then 2% methanol/methylene chloride and finally 5% methanol/methylene chloride and obtain a mixture of the title compounds.

Prepare the hydrochloride salt by reacting the title compounds with about 1.1 eq. of 0.1N hydrochloric acid.

EXAMPLE 22

1-[6-(2-chloro-4-methoxyphenoxy)hexyl]pyrrolidine

Stir overnight at room temperature 500 mg. of the iodide prepared in Example 2 or 3, 5 ml. acetonitrile, 967 mg. pyrrolidine and 3 gm. cesium carbonate in a reaction flask. Add methylene chloride and wash with water, remove the solvent and excess reactants to recover the title compound.

Prepare the hydrochloride salt by reacting the title compound with 1.1 eq. of 0.1N hydrochloric acid.

EXAMPLE 23

1-[6-(1-imidazolyl)hexyl]imidazole (a) Heat the reflux for 20 minutes, 5 gms. of 1,6-dibromohexane, 15 ml. acetone and 15.2 gms. sodium iodide. Treat with a water wash in methylene chloride then remove the solvent to recover 1,6-diiodohexane.

(b) Stir overnight at room temperature 1 gm. of the diiodo compound from step (a), 10 ml. DMF and 2.67 gm. sodium imidazole. Treat with methylene chloride and wash with water, dry and remove the solvent to recover the title compound as a crystalline material.

Prepare the hydrochloride by reacting the title compound with about 1 eq. of 0.1N hydrochloric acid.

EXAMPLE 24

Sodium 1-[6-(2-chloro-4-methoxyphenoxy)hexyl]1,4-dihydro-4-oxo-7-methyl-1,8-naphthyridine-3-carboxylate Stir overnight at room temperature 1 gm. of the iodide prepared in Examples 2 or 3, 10 ml. DMF, 834 mg. 4-hydroxy-7-methyl-1,8-naphthyridine-3-carboxylic acid and 326 mg. sodium hydroxide in a reaction flask. Wash with water in methylene chloride. Elute on a coarse silica column with methylene chloride then 3% methanol/methylene chloride to isolate the title compound as the carboxylic acid.

Prepare the sodium salt of the title compound by reaction with 0.1N sodium hydroxide.

EXAMPLE 25

1-[6-(2-methyl-1-imidazolyl)hexyl]-2-methylimidazole

Stir overnight at room temperature, 10 ml. DMF, 1.18 gm. sodium hydroxide, 2.43 gm. 2-methyl imidazole and 1 gm. 1,6-diiodohexane in a reaction flask. Treat with methylene chloride and wash with water. Dry on sodium sulfate and remove the solvent to yield the title compound.

Prepare the hydrochloride salt of the title compound by reacting with about 1 eq. of 0.1N hydrochloric acid.

EXAMPLE 26

Mixture of 1-[6-(2-chloro-4-methoxyphenoxy)hexyl]-3-and-5-pyrazole

Stir overnight at room temperature, 1 gm. of the iodide prepared in Examples 2 and 3, 10 ml. DMF, 0.656 ml. (3 eq.) 3-methylpyrazole and 348 mg. sodium hydroxide in a reaction flask. Add methylene chloride and wash several times with water, dry and remove solvent to obtain a mixture of the title compounds.

The title compounds do not form water soluble salts.

EXAMPLE 27

9-[6-(2-chloro-4-methoxyphenoxy) hexyl]purine and 7-[6-(2-chloro-4-methoxyphenoxy)hexyl]purine Stir overnight at room temperature, 300 mg. of the iodide prepared in Examples 2 and 3, 3 ml. DMF, 147 mg. purine and 49 mg. sodium hydroxide in a reaction flask. Add methylene chloride and wash with water. Elute on a coarse silica column with methylene chloride, then 2% methanol/methylene chloride, then 4 and 5% methanol/methylene chloride to obtain a major amount of the 9-substituted title compound and a minor amount of the 7-substituted title compound.

The title compounds do not form water soluble salts.

EXAMPLE 28

1-[6-(2-chloro-4-methoxyphenoxy)hexyl]-4-methyl-5-hydroxymethylimidazole and
1-[6-(2-chloro-4-methoxyphenoxy)hexyl]-5-methyl-4-hydroxymethylimidazole Stir for about 9 hours at room temperature 25 ml. DMF, 5 gm. sodium hydroxide, 3.5 gms. 4-hydroxymethylimidazole and 3.0 gms of the iodide prepared in Examples 2 and 3 in a reaction flask. Partition with water/methylene chloride. Elute on a silica column with 100% methylene chloride then 8% methanol in methylene chloride to obtain a mixture of the title compounds. NMR (nuclear magnetic resonance) indicates two isomers are present.

Separate the isomers on a silica column with 50/50 THF/ethylacetate. Recover one isomer as the top spot and the other isomer as the bottom spot.

Prepare the hydrochloride of each title compound by reacting with about 1 eq. of 0.1N hydrochloric acid. MS: m/z 353 ($M^+$) Both isomers, free base $H^1$-NMR-200 mHz $^\delta H(CDCl_3)$, 1.3–1.7 (4H,m), 1.7–2.0 (4H,m), 2.22 (3H, broad s), 3.78 (3H,s) 3.85 (2H,t,J 7Hz) , 4.00 (2H,t,J 7Hz) , 4.6 (2H,s,5 or 4 —$CH_2OH$) , 4.65,s,4 or 5—$CH_2OH$), 6.7–7.0 (3H,m), 7.4 (1H,s)

EXAMPLE 29

1-[6-(2-chloro-4-methoxyphenoxy)hexyl]-2-ethylimidazole

Stir at room temperature for four days 2 gms. of the iodide prepared in Examples 2 or 3, 2 gms. of 2-ethylimidazole, 2.5 ml. DMF and 0.4 gm sodium hydroxide in a reaction flask. Remove the solvent and partition with water/methylene chloride. Elute on a silica column with 100% methylene chloride and then 10% methanol to yield the title compound. MS:m/z 337 ($M^+$) $H^1$-NMR-200 mHz, $^\delta H$ ($CDCl_3$), 1.34 (3H,t,J 7.5 Hz), 1.3–1.65 (4H,m), 1.70–1.90 (4H,m) 2.66 (2H,q,J 7.5Hz), 3.75 (3H,s), 3.83 (2H,t,J 7Hz), 3.95 (2H,t,J 6Hz), 6.7–7.0 (5H,m).

Prepare the hydrochloride salt by reacting with about 1.1 eq. of 0.1N hydrochloric acid.

EXAMPLE 30

2-[6-(2-chloro-4-methoxyphenoxy)-1-hexylthio]-benzimidazole

Stir at room temperature for four days 2.5 gms. 2-mercapto-benzimidazole, 2 gms. of the iodide prepared in Examples 2 or 3, 25 ml. DMF and 0.71 gm. sodium hydroxide in a reaction flask. Remove the solvent and partition with water/methylene chloride. Elute on a silica column with 100% methylene chloride then 50/50 ethylacetate/methylene chloride to obtain the title compound. MS: m/z 391 ($M^+$) $H^1$-NMR-200 mHz-$^\delta H$ ($CDCl_3$), 1.5–1.6 (4H,m), 1.7–1.9 (4H,m), 3.35 (2H,t,J 7Hz), 3.75 (3H,s) 3.95 (2H,t,J 6Hz), 6.7–7.0 (3H,m), 7.2–7.4 (4H,m), 7.65–7.75 (1H,m).

EXAMPLE 31

1-[6-(2-chloro-4-methoxyphenoxy)hexyl]-4-methyl-2-ethylimidazole and
1-[6-(2-chloro-4-methoxyphenoxy)hexyl]-5-methyl-2-ethylimidazole Stir for four days at room temperature 2 gms of 2-ethyl-4-(5)-methylimidazole, 3 gms. of the iodide prepared in Examples 2 or 3, 0.75 gms. sodium hydroxide and 25 ml. DMF in a reaction flask. Remove the solvent and partition with water/methylene chloride. Elute on a silica column with 100% methylene chloride then 5% methanol to obtain a 70:30 weight ratio of the title compounds as evidenced by NMR of their hydrochloride salts.

Prepare the hydrochloride salts by reaction with 1 eq. of 0.1N HCl.

MS: M/z 351 ($M^+$) HCl salt, $H^1$-NMR-200 mHz-$^\delta H$ ($CDCl_3$) , 1.2–1.7 (7H,m) , 1.7–2.0 (4H,m), 2.32 (3H,s, isomeric 4—$CH_3$) , 2.40 (3H,s,isomeric 5—$CH_3$), 3.05 (2H,q,J 8Hz), 3.75 (3H,s), 3.90–4.05 (4H,m), 6.7–7.1 (4Hz).

EXAMPLE 32

1-[3-(2-chloro-4-methoxyphenoxy)propyl]imidiazole (a) Prepare 1-[3-(2-chloro-4-methoxyphenoxy)propyl] bromide by reacting 10 gm of 2-chloro-4-methoxyphenol, 51 gm of 1,3-dibromopropane, 35 gm $K_2CO_3$ in 60 ml acetone under reflux for 48 hours. Remove acetone by distillation. Extract residue with methylene chloride and filter. Remove solvent and distill residue under vacuum to recover the product, b.p. 150°–160° C. at 0.5 mm Hg.

(b) Stir for 18 hours at room temperature, 1 gm of the bromide prepared in step (a), 2 gms. imidazole, 1.2 gm. sodium hydroxide and 10 ml. DMF in a reaction flask. Remove the solvent and partition with water/methylene chloride to obtain the title compound.

Prepare the hydrochloride salt by reacting the title compound with about 1 eq. of 0.1N HCl. Purify the salt in methylene chloride/water.

FAB-MS: m/z 267 ($M^+$) , HCl salt, $H^1$-NMR-200 mHz, $^\delta H$ ($CDCl_3$), 2.48 (2H,m), 3.76 (3H,s), 4.00 (2H,t,J 5.5 Hz), 4.63 (2H,t,J 6.8 Hz), 6.72–7.00 (3H,m), 7.24 (1H,s), 7.36 (1H,s) 9.68 (1H,s).

EXAMPLE 33

2-[7-(2-chloro-4-methoxyphenoxy)heptyl]-1-methylimidazole

Add 196 mg. 1,2-dimethylimidazole and 5 ml. freshly distilled THF to a dry reaction flask, cool to –78° C. then add 0.81 ml. of 2.5 molar n-butyl lithium in hexane, stir 15 minutes at –78° C., then add 0.5 gms of the iodide prepared in Examples 2 and 3 and 5 ml THF and stir for two hours while slowly warming to room temperature.

Stir the reaction mixture overnight at room temperature. Add 5 ml. water, remove the solvent, then add methylene chloride and wash with water, dry over sodium sulfate then elute on a coarse silica column with methylene chloride then 3% ethanol/methylene chloride to obtain the title compound.

Prepare the hydrochloride salt of the title compound by reacting with about 1.1 eq. of 0.1N hydrochloric acid.

EXAMPLE 34

2-[7-(2-chloro-4-methoxyphenoxy)heptyl]imidazole (a) Prepare 2-methyl-1-triphenylmethylimidazole by refluxing 1.75 gms. 2-methylimidazole, 10 ml. THF and 2 gms. trityl chloride overnight. Recover the product as follows: Add methylene chloride, wash with water, then elute on a coarse silica column with methylene chloride followed by 5% methanol/methylene chloride.

(b) Prepare the title compound as follows: Add 500 mgs. of the compound of step (a) to 10 ml. dry THF then cool to –78° C., add over 3–5 minutes 0.61 ml. n-butyl lithium, then add 376 mg. of the iodide prepared in Examples 2 and 3 in 3 ml. THF over 5 minutes. Stir overnight while slowly warming to room temperature. Remove about 80 to 90% of the solvent, add methylene chloride, wash with water, then brine, and dry over sodium sulfate. Elute on a coarse silica column with methylene chloride, then 10% ethylacetate/ methylene chloride, and finally 20% ethylacetate/methylene chloride. Treat the resulting product with 15 ml. formic acid and heat to 100° C. for 1.5 hours, let cool to room temperature and a white precipitate forms. Remove the formic acid and neutralize with 10% sodium hydroxide solution to recover the title compound.

Prepare the hydrochloride salt by reacting the title compound with about 1 eq. of 0.1N HCl.

EXAMPLE 35

2-[7-(2-chloro-4-methoxyphenoxy)heptyl]-1-butylimidazole

Stir overnight at room temperature, 79 mgs. of the compound prepared in Example 34, 2 ml. DMF, 29.4 ml. sodium hydroxide and 44.8 mg. n-butyl iodide in a reaction flask. Add methylene chloride and wash with water. Elute on a coarse silica column with 2% methanol/methylene chloride then 3% methanol/methylene chloride and finally 5% methanol/methylene chloride to isolate the title compound.

Prepare the hydrochloride by reacting the title compound with about 1 eq. of 0.1N HCl.

EXAMPLE 36

1-[6-(4-phenoxyphenoxy)hexyl]imidazole (a-1) Prepare 6-(4-phenoxyphenoxy)hexyl-1-bromide by adding together in a reaction flask at room temperature, 25 ml. DMSO (dimethylsulfoxide), 5 gm. p-phenoxyphenol, 6 gm. of 0.1074 moles potassium hydroxide and 13.1 gm. 1,6-dibromohexane. The reaction is exothermic and a solid results. Add 25 ml. more of DMSO and stir 45 minutes to yield the desired bromide.

(a-2) Add to a reaction flask 10 ml. DMSO, 1.2 gm. powdered KOH, 4.9 ml. 1,6-dibromohexane and 1 gm. solid p-phenoxyphenol. The reaction is exothermic. Add methylene chloride and wash with water. Elute on a coarse silica column with 10% methylene chloride/hexane, then 20% methylene chloride/hexane, the 30% methylene chloride/ hexane and finally 40% methylene chloride/hexane to isolate the desired bromide compound.

(b) Heat to reflux for 10 minutes, 1.4 gm. of the compound prepared in step (a-1) or (a-2), 3 gms. sodium iodide and 20 ml. acetone in a reaction flask. Remove the acetone, add methylene chloride, wash with water then brine and dry over sodium sulfate. Remove the solvent and the desired product, 6-(4-phenoxyphenoxy)hexyl-1-iodide, crystallizes.

(c) Stir for about 48 hours at room temperature 300 mg. of the iodide from step (b), 5 ml. DMF and 204 mg. sodium imidazole in a reaction flask. Add methylene chloride and wash with water, then brine and dry over sodium sulfate. Dissolve in methylene chloride and filter to obtain the title compound.

Prepare the hydrochloride salt by reaction with about 1.1 eq. of 0.1N HCl.

EXAMPLE 37

Dimethyl 1-[6-(2-chloro-4-methoxyphenoxy)hexyl]-4,5-imidazole dicarboxylate

Stir for 24 hours at room temperature 3.7 gm. dimethyl 4,5-imidazole dicarboxylate, 3.7 gm. of the iodide prepared in Examples 2 or 3, 25 ml. DMF and 2.8 gm potassium carbonate. Remove the solvent, extract the residue with methylene chloride, filter, wash methylene chloride fractions with water, elute on a silica column with 100% methylene chloride then 10% methanol/methylene chloride to recover the title compound.

Free base $H^1$-NMR-200 mHz, $\delta H$ (CDCl$_3$) 1.3–1.7 (4H, m), 1.7–1.9(4H,m), 3.75 (3H,s), 3.92(6H,s), 3.95 (2H,t,J 8Hz), 6.7–7.0 (3H,m), 7.55 (1H,s)

EXAMPLE 38

1-[6-(2-chloro-4-methoxyphenoxy)hexyl]-4,5-di(hydroxymethyl)imidazole

Add 1 gm. of the compound prepared in Example 37 to 20 ml. THF (dry N$_2$) cool to 0° C. and slowly add Li(C$_2$H$_5$)$_3$BH and stir for about 30 minutes. Warm to room temperature and stir for about 90 minutes. Add 2 ml. concentrated hydrochloric acid, stir for about 30 minutes and then add sufficient 50% sodium hydroxide to neutralize the acid and obtain a pH of 10–11. Filter to remove the solid. Add 75 ml. THF, 2 ml. 50% NaOH, 3 ml. of 30% hydrogen peroxide and stir for about one hour. Add 30 ml. saturated NaCl solution and 50 ml. methylene chloride. Dry the resulting organic layer with sodium sulfate and evaporate to obtain the title compound.

FAB-MS: m/z 369 (M$^+$) , HCl salt, $H^1$-NMR-200 mHz, $\delta H$ (CDCl$_3$), 1.3–1.6 (4H,m), 1.6–2.0 (4H,m), 3.72 (3H,s), 3.93 (2H,t,J 6Hz), 4.25 (2H,t,J 8Hz), 4.64 (2H,s), 4.68 (2H,s), 6.7–6.9 (3H,m), 8.95 (1H,s).

EXAMPLE 39

Trans 1-[(2-chloro-4-methoxyphenoxy)methyl]4-[(1-imidazolyl)methyl]cyclohexane (a) Add 14.5 gm. of trans 1,4-bis hydroxymethyl cyclohexane to 250 ml. methylene chloride and add 20 ml. methanesulfonyl chloride, cool to 0° C. and slowly add 36 ml. triethylamine over a period of one hour. Remove the solvent, extract with water, filter and wash with methanol to obtain trans 1,4-bis mesylate methyl cyclohexane.

(b) Add 30 gms. of the mesylate prepared in step (a) to 300 ml. methylethyl ketone (MEK), then add 90 gm. sodium iodide and reflux for about 30 minutes. Remove the solvent and extract with methylene chloride to yield trans 1,4-bis iodomethyl cyclohexane.

(c) Add 3 gms. of 2-chloro-4-methoxyphenol, 15 gms. of the diiodo compound prepared in step (b), 100 ml. water, 100 ml. methylene chloride in a reaction flask, add 0.5 gm (n-butyl) ammonium sulfate and 25 ml 50% aqeuous NaOH. Elute on a silica column. A mixture of mono and bis ether results as evidenced by NMR.

Add the resulting mixture to 3 gm. sodium imidazole in 20 ml. DMF. Stir at room temperature for about 48 hours. Remove the solvent and elute on a silica column with 100% methylene chloride then 5% methanol to yield the title compound.

Prepare the hydrochloride salt by reaction with 0.1N HCl.

FAB-MS: m/z 335 (M$^+$) HCl salt, H$^1$-NMR-200 mHz, $^\delta$H (CDCl$_3$), 0.9–1.30 (4H,m), 1.6–2.1 (6H,m), 3.75 (3H,s), 3.77 (2H,d,J 6Hz), 4.2 (2H,d,J 6Hz), 6.7–7.0 (3H,m), 7.14 (1H,s), 7.43 (1H,s), 9.55 (1H,s).

EXAMPLE 40

1-(9,9-dimethyl-dec-7-ynyl)-imidazole (a) Add 5 ml. freshly distilled THF and 413 mg. 3,3-dimethyl-1-butyne to a dry reaction flask, cool to −78° C. then add 2.01 ml. n-butyl lithium (2.5M in hexane), stir about 30 minutes at −78° C., transfer into 3 ml. THF and 4.9 gm. 1,6-dibromo hexane at 0° C., stir 6 hours and add 2 ml. dry DMSO to form a precipitate. Wash with water, in methylene chloride. Elute through a short bed of silica with hexane to remove polar material giving a mixture of 1,6-dibromo hexane and 1 bromo-(9,9-dimethyl-dec-7-yne.

(b) Stir overnight at room temperature 4.73 gm. of the mixture prepared in step (a), 5 ml. DMF and 2.1 gm. sodium imidazole, in a reaction flask. Add methylene chloride, wash with water, then brine and dry over sodium sulfate. Elute on a coarse silica column with methylene chloride, then 2% methanol/methylene chloride. Combine fractions containing product and chromatograph on a coarse silica column with 25% ethylacetate/methylene chloride, then 35% ethylacetate/methylene chloride to isolate the title compound.

Prepare the hydrochloride salt by reaction with about 1.1 eq. of 0.1N HCl.

EXAMPLE 41

1-[6-(2-chloro-4-methoxyphenoxy)hexyl]-3-methylimidazolium iodide

Stir at room temperature for about 2.5 hours, 300 mg. of the compound prepared in Example 1, 5 ml. methylene chloride and 0.066 ml. methyl iodide. Elute on a coarse silica column with methylene chloride, then 5% methanol/methylene chloride and finally 10% methanol/methylene chloride, to isolate the title compound.

EXAMPLE 42

1-[6-(2-chloro-4-methoxyphenoxy)hexyl]-4and 5-aminomethyl imidazole

Stir overnight at room temperature, 0.5 gm NaOH, 20 ml. DMF, 4(5) triphenylmethylaminomethyl imidazole and the iodide prepared in Examples 2 and 3, in a reaction flask. Remove the solvent and partition with methylene chloride/water, then brine. Elute on a silica column with 100% methylene chloride, then 40% ethylacetate. Two fractions (the top spot and the bottom spot) containing the trityl protected title compounds separate.

Recover each of the title compounds as follows:

Add the desired fraction to 20 ml. formic acid/2 ml. methylene chloride in a reaction flask and stir overnight at room temperature. Remove all volatiles, partition with 1% HCl H$_2$O/hexane then add 50% NaOH to a pH over 10. Partition with water/methylene chloride. Elute the methylene chloride residue on a silica column with methylene chloride, then 20% methanol in CH$_2$Cl$_2$ to yield the desired title compound. The ratio of the top spot fraction compound to the bottom spot fraction compound is about 4 to 1.

Prepare the hydrochloride salt of each title compound by reaction with about 1 eq. of 0.1N HCl.

(4 or 6 NH$_2$—CH$_2$—), free base FAB-MS: m/z 338 (M$^+$); H$^1$-NMR-200 mHz, $^\delta$H (CDCl$_3$), 1.3–1.55 (6H,m), 1.60–1.9 (4H,m), 3.75 (3H,s), 3.85 (2H,s), 3.9–4.2 (4H,m), 6.7–7.0 (4H,m), 7.45 (1H,s).

(4 or 5 NH$_2$—CH$_2$—), HCl salt FAB-MS: m/z 338(M$^+$) H$^1$-NMR-200 mHz, $^\delta$H (CDCl$_3$), 1.3–1.7 (4H,m), 1.7–1.9 (4H,m), 3.75 (3H,s), 3.9–4.0 (4H,m), 4.08 (2H,s), 6.7–7.0 (3H,m), 7.28 (1H,s), 7.52 (1H,s).

EXAMPLE 43

1-[6-(2-chloro-4-methoxyphenoxy)hexyl]-4,5-dimethyl imidazole (a) Prepare 1-[6-(2-chloro-4-methoxyphenoxy)hexyl]-4(5)-methyl-5(4)-hydroxymethyl imidazole as follows: Add 3 gm of 6(2-chloro-4-methoxyphenoxy)hexyl-1-iodide prepared in Example 1, 2.5 gm 4-hydroxymethyl-5-methyl imidazole, 1 gm NaOH to 25 ml DMF (dimethylformamide), stir for 48 hours. Remove DMF by high vacuum, partition with H$_2$O/CH$_2$Cl$_2$, purify methylene chloride residue on silica column with 100% methylene chloride then 10% CH$_3$OH/CH$_2$Cl$_2$ to give the product.

(b) Stir overnight at room temperature the compound prepared in step (a) and 30 ml. thionyl chloride. Heat to reflux for 5 minutes then remove the SOCl$_2$ and chase with toluene.

(c) Add 50 ml. THF to the product prepared in step (b) and cool to 0° C., add 12 ml. (1 eq.) triethyl lithium borohydride and stir for 10 minutes, warm to room temperature and stir for one hour. Add 20 ml. 10% sodium hydroxide then 6 ml. 30% H$_2$O$_2$, stir for one hour, add saturated NaCl solution and wash with saturated NaCl solution twice. Dry with sodium sulfate, remove THF and elute on a silica column with methylene chloride, then 2% methanol to obtain the title compound.

Prepare the hydrochloride salt by reaction with about 1 eq. of 0.1N HCl.

FAB-MS: m/z (337M$^+$) HCl salt H$^1$-NMR-200 mHz, $^\delta$H(CDCl$_3$), 1.35–1.7 (4H,m), 1.7–2.0 (4H,m), 2.22 (3H,s), 2.38 (3H,s), 3.78 (3H,s), 3.98 (2H,t,J 5Hz), 4.15 (2H,t,J JHz), 6.7–7.0 (3H,m), 8.95 (1H,s).

EXAMPLE 44

1-[6-(2-chloro-4-methoxyphenoxy)hexyl]-2-hydroxymethyl imidazole

Add 50 ml. of 37% formaldehyde to 3 gms. of the compound prepared in Example 1, in a Paar bomb and purge with nitrogen. Heat in an oil bath at 130° C. for 16 hours. Remove all liquids under vacuum. Partition with 10% sodium hydroxide/methylene chloride then water/methylene chloride. Elute on a silica column with methylene chloride then 8% methanol to obtain the title compound.

Prepare the hydrochloride salt by reaction with about 1 eq. 0.1N HCl.

FAB-MS: m/z 339(M$^+$HCl salt, H$^1$-NMR-200 mHz, $^\delta$H(CDCl$_3$), 1.3–1.7 (4H,m), 1.7–2.0 (4H,m), 3.75 (3H,s), 3.96 (2H,t,J 6Hz), 4.24 (2H,t,J 8Hz), 5.02 (2H,s) 6.7–7.0 (3H,m), 7.12 (1H,d,J 2Hz), 7.34 (1H,d,J 2Hz).

EXAMPLE 45

1-allyloxycarbonylmethyl-2-[7-(2-chloro-4-methoxyphenoxy)heptyl]imidazole

Stir overnight at room temperature 4 gms. of the compound produced in Example 34, 20 ml. dry DMF, 545 mg. powdered sodium hydroxide, 2.8 gms. slowly added allyl iodo acetate. Add methylene chloride and wash with water, then brine and dry over sodium sulfate. Elute on a coarse silica column with methylene chloride, then 20% methanol/$CH_2Cl_2$ and finally with 5% methanol/methylene chloride to isolate the title compound.

Prepare the hydrochloride salt by reaction with about 1 eq. of 0.1N HCl.

EXAMPLE 46

1-carboxymethyl-2-[7-(2-chloro-4-methoxyphenoxy)heptyl]imidazole

Stir for 3 hours at room temperature a mixture of 100 mg. of the compound made in Example 45, 2 ml. THF and 0.2 ml. of 10% NaOH solution. Adjust the pH to about 7.

Add methylene chloride. Remove all water and solvents to obtain a white solid. Add $CH_2Cl_2$, stir and filter solids. Recover the title compound.

EXAMPLE 47

1-[6-(2-chloro-4-methoxyphenoxy)hex-2-ynyl]imidazole (a) Add 30 ml. THF and 10 ml. DMSO to a reaction flask and cool to −78° C. Add 7.4 ml. n-butyl lithium (2.5M/hexane), stir for five minutes and add 2.6 gms. of tetrahydropyran protected propargyl alcohol and warm to room temperature. Stir 5 minutes and add 3 gms. of 1-(2-chloro-4-methoxyphenoxy)propyl-3-bromide resulting in a slightly exothermic reaction. Stir for about 1.5 hours. Remove the THF by vacuum and partition with water/methylene chloride. Elute the methylene chloride residue on a silica column with 25% methylene chloride/hexane then 50/50 methylene chloride/hexane. Add the resulting product to 50/25/25 THF/$H_2O$/$CH_3OH$ and add 1 gm. para toluene sulfonic acid. Stir overnight, remove THF/methanol, partition with 5% $NaHCO_3$/$CH_2Cl_2$ then with water/methylene chloride. Remove the $CH_2Cl_2$ to obtain the desired product, 1-hydroxy-6-(2-chloro-4-methoxyphenoxy)hex-2-yne.

(b) Add 25 ml. thionyl chloride to 1.17 gms. of the compound prepared in step (a) and reflux for 1 hour. Remove the thionyl chloride. Add 25 ml. DMF and 3 gms. sodium imidazole and stir overnight. Remove the DMF and partition with $H_2O$/$CH_2Cl_2$.

Elute on a silica column with 100% $CH_2Cl_2$ then 100% ethylacetate to obtain the title compound.

Prepare the hydrochloride salt by reaction with about 1 eq. of 0.1N HCl.

FAB-MS: m/z 305 HCl salt, $H^1$-NMR, 200 mHz, $\delta H(CDCl_2)$, 2.05 (2H,m), 2.55 (2H,m), 3.78 (3H,s), 4.08 (2H,t,J 5Hz), 5.20 (2H,m), 6.7–7.0 (3H,m), 7.30 (1H,s), 7.38 (1H,s), 9.6 (1H,s).

EXAMPLE 48

1-acetamido-2-[7-(2-chloro-4-methoxyphenoxy)heptyl]imidazole

Add 100 mg. of the compound prepared in Example 45 and 5 ml. methylene chloride to a reaction flask. Saturate with ammonia gas at room temperature. Let sit for about 30 minutes. TLC with 5% methanol/$CH_2Cl_2$ indicates a more polar product is in about 50% of the mixture. Stir for about 2 hours, add sodium ethoxide in ethanol, then ammonia and stir for about 1.5 hours. Recover the title compound on TLC.

Prepare the hydrochloride salt by reaction with about 1 eq. of 0.1N HCl.

EXAMPLE 49

1-(2-hydroxyethyl)-2-[7-(2-chloro-4-methoxyphenoxy)heptyl]imidazole

Add 100 mg. of the compound prepared in Example 45, 5 ml. THF and excess lithium aluminum hydride to a reaction flask and stir about 20 minutes. Add ethylacetate, water and ammonium chloride and let sit overnight at room temperature.

Extract with ethylacetate and elute on a coarse silica column with methylene chloride, then 5% methanol/methylene chloride and finally 10% methanol/methylene chloride. The title compound is recovered. Prepare the hydrochloride salt by reaction with about 1 eq. of 0.1N HCl.

EXAMPLE 50

1-(8-phenyl-oct-7-ynyl)imidazole (a) Prepare 6-phenylethynylhexyl-1-bromide by adding 1.07 ml phenylacetylene to 10 ml of THF in a reaction flask, cool to −78° C. then add 3.9 ml n-BuLi (2.5 molar in hexane), stir 5 minutes, warm to 0° C. and add 45 ml of 1,6-dibromohexane and 5 mol of dry DMSO. Stir at room temperature for 1.5 hours, remove solvent and treat with methylene chloride and water to recover the product.

(b) Stir for 48 hours at room temperature in a reaction flask, 1.65 gms of the product of step (a) and 1.68 gm sodium imidazole in 5 ml DMF. Remover the resulting title compound by treating with methylene chloride, washing with water and drying over sodium sulfate. Then elute on a coarse silica column with 100% methylene chloride followed by 2% $CH_3OH$/$CH_2Cl_2$ to yield the title compound.

Prepare the hydrochloride salt by reaction with 0.1N HCl.

MS: m/z 253 ($M^+$) HCl salt.

EXAMPLE 51

1-[6-hydroxy-6-(2-chloro-4-methylphenyl)hexyl]imidazole (a) Prepare 6-(2-chloro-4-methoxyphenyl)6-oxo-hexyl-1-bromide by adding 200 ml methylene chloride, 5.87 ml m-chlorotoluene and 11.7 g 6-bromohexanoyl chloride to a reaction flask, then adding 7.95 g aluminum chloride. Stir 3 hours. Wash with water, sodium bicarbonate, water and brine, dry over sodium sulfate then elute on a coarse silica column with 100% hexane, 10% methylene chloride/hexane, 15% methylene chloride/hexane and 20% methylene chloride/hexane to yield the product.

(b) Prepare 1[6-hydroxy-6-(2-chloro-4-methylphenyl)hexylbromide by adding 1 gm of the product of step (a), 10 ml ethanol and 124 mg sodium borohydride. Stir 1 hour at room temperature. Remove the solvent, add methylene chloride, wash with water, brine and dry to recover the product.

(c) Stir for 96 hours in a reaction flask 975 mg of the product of step (b), 10 ml DMF and sodium imidazole. Treat with methylene chloride, wash with water, then brine, dry over sodium sulfate then elute on a coarse silica column with methylene chloride then 3% methanol/methylene chloride to yield the title compound.

Prepare the hydrochloride salt of the title compound by reaction with 0.1N HCl.

FAB MS: m/z 293 ($M^+$)—HCl salt.

EXAMPLE 52

1-[7-oxy-7-(4-methoxyphenyl)heptyl]imidazole (a) Prepare 7-(4-methoxyphenyl-7-oxo)heptyl-1-bromide by stirring for one hour at room temperature, 2.16 gm anisole, 100 ml methylene chloride, 7-bromoheptanoyl chloride and aluminum chloride. Wash with water, sodium bicarbonate solution, water then brine. Dry over sodium sulfate. Elute on a coarse silica column with hexane then methylene chloride/hexane to recover the product.

(b) Heat to reflux for 45 mins. 0.5 gm of the product of step (a), 10 ml MEK (methylethylketone) and 1.25 gm sodium iodide. Remove most of the MEK, add methylene chloride, then wash with water, followed by brine and dry over sodium sulfate to give the iodide of the compound prepared in step (a). Add 450 mg of sodium imidazole in 10 ml DMF and stir for 48 hours. Add methylene chloride, wash with water, then wash with brine and dry over sodium sulfate to yield the title compound.

Prepare the hydrochloride salt by reaction with 0.1N HCl.

FAB-MS: m/z 287 ($M^+$)—HCl salt.

EXAMPLE 53

1-[7-hydroxy-7-(4-methoxyphenyl)heptyl]imidazole

Stir at room temperature for 2.5 hours, 1 gm of the compound prepared in Example 52(b), 10 ml ethanol and 0.5 gm sodium borohydride. Remove most of the ethanol, add methylene chloride and wash with water, elute on a coarse silica column with methylene chloride then 3% methanol/methylene chloride to obtain the title compound.

MS: m/z 288 ($M^+$)-base.

EXAMPLE 54

1-[7-(4-methoxyphenyl)-hept-6-enyl]-imidazole hydrochloride

Treat the compound prepared in Example 53 with 1.1 eq. of 0.1N HCl to give the title compound.

FAB/Gly-Thio-MS: m/z 271 ($M^+$) HCl salt.

EXAMPLE 55

1-[7-hydroxyimino-7-(4-methoxyphenyl)heptyl]imidazole

Stir overnight at room temperature 0.5 gm of the compound prepared in Example 52(b), 10 ml ethanol, 1 ml water and a large excess of hydroxyl amine.HCl and stir for 4 hours. Remove most of the ethanol by bubbling nitrogen through the reaction mixture. Adjust the pH to about 10 with 10% aqueous NaOH, add methylene chloride and wash with water, then brine and dry over sodium sulfate. Then elute on a coarse silica column with methylene chloride then 1, 2, 3 and 4% methanol/methylene chloride to give the title compound.

Prepare the hydrochloride salt by reaction with 1.1 eq. of 0.1N HCl.

MS: m/z 302 ($M^+$) HCl salt.

EXAMPLE 56

1-[7-(4-methoxyphenyl)heptyl]imidazole

Shake overnight under 30 psi hydrogen pressure, 87 mg of the free base of the compound prepared in Example 54, 20 ml anhydrous ethanol and PtO. Filter and remove the ethanol then elute on a coarse silica column with methylene chloride then 2% methanol/methylene chloride to obtain the title compound.

Prepare the hydrochloride salt by reaction with 1.1 eq. of 0.1N HCl.

MS: m/z 272 ($M^+$) HCl salt.

EXAMPLE 57

1-[7-oxo-7-(4-methylthiophenyl)heptyl]imidazole (a) Prepare 7-(4-methylthiophenyl-7-oxo)heptyl-1-bromide by stirring for 2.5 hours, 2.34 ml thioanisole, 5 gm 7-bromoheptanoylchloride and 3.19 aluminum chloride in 100 ml methylene chloride at room temperature. Slowly add water then wash with water, sodium bicarbonate solution, water and brine. Elute on a coarse silica column with 40% methylene chloride/hexane then 50% methylene chloride/hexane to give the product as white crystals.

(b) Add 100 ml acetone and 6.5 gm sodium iodide to the product of step (a) and heat to reflux for 1.5 hours, remove the solvent. Treat with methylene chloride and wash with water to obtain the iodide of the compound produced in step (a).

(c) Add 30 ml of DMF to the compound produced in step (b), add sodium imidazole and stir overnight. Treat with methylene chloride and wash with water, then elute on a coarse silica column with methylene chloride then 3% methanol/methylene chloride to yield the title compound.

Make the hydrochloride salt by reaction with 0.1N HCl.

FAB/Gly-Thio-MS: m/z 303 ($M^+$) HCl salt.

EXAMPLE 58

1-[7-hydroxyimino-7-(4-methylthiophenyl)heptyl imidazole

Stir for 5 hours at room temperature 300 mg of the compound produced in Example 57(c), 10 ml ethanol, 1 ml water and 344 mg hydroxylamine.HCl. Bubble nitrogen through the reaction mixture to remove the ethanol, add methylene chloride and wash with 10% sodium hydroxide, water, then brine to yield the title compound.

Prepare the hydrochloride salt by reaction with 0.1N hydrochloric acid.

FAB/Gly-Thio-MS: m/z 318 ($M^+$) HCl salt.

EXAMPLE 59

1-[7-hydroxy-7-(4-methylthiophenyl)heptyl]imidazole

Stir at room temperature for 2 hours, 200 mg of the compound prepared in Example 57, 5 ml ethanol and 50 mg sodium borohydride. Remove the ethanol with nitrogen, add methylene chloride then wash with water then brine and dry over sodium sulfate to obtain the title compound.

Make the hydrochloride salt by reaction with 1.2 eq. of 0.1N HCl.

FAB/Gly-Thio-MS: m/z 305 (M$^+$) HCl salt.

EXAMPLE 60

1-[7-oxo-7-(4-methylsulfonylphenyl)heptyl]imidazole

To 1 gm of the compound prepared in Example 57 and 20 ml acetic acid slowly add over one hour 6 ml 30% hydrogen peroxide and let stand at room temperature for 3.5 hours.

Add 10% sodium hydroxide in methylene chloride, wash with water, then brine and remove the solvent to obtain the title compound.

FAB/Gly-Thio-MS: m/z 335 (M$^+$) HCl salt.

EXAMPLE 61

1-[7-methoxyimino-7-(4-methylsulfonyl-phenyl)heptyl]imidazole

Stir for 4.5 hours at room temperature, 100 mg of the compound produced in Example 60, 5 ml ethanol, 0.5 ml water and 125 mg methoxyamine hydrochloride. Remove most of the ethanol with nitrogen, add methylene chloride and 10% sodium hydroxide. Wash with water, then brine and dry over sodium sulfate to obtain the title compound.

Prepare the hydrochloride salt by reaction with 1.1 eq. of 0.1N HCl.

FAB/Gly-Thio-MS: m/z 364 (M$^+$) HCl salt.

EXAMPLE 62

1-[7-hydroxyimino-7-(4-methylsulfonyl-phenyl)heptyl]imidazole

Stir for 5 hours at room temperature 130 mg of the compound prepared in Example 60, 5 ml ethanol, 0.5 ml water and 135 mg hydroxylamine hydrochloride. Remove the ethanol with nitrogen, add methylene chloride, 10% sodium hydroxide, wash with water then brine and dry over sodium sulfate to obtain the title compound.

Prepare the hydrochloride salt by reaction with 1.1 eq. of 0.1N HCl.

FAB/Gly-Thio-MS: m/z 350 (M$^+$) HCl salt.

EXAMPLE 63

1-[7-hydroxy-7-(4-methylsulfonyl-phenyl)heptyl]imidazole

Stir for 3 hours at room temperature, 150 mg of the compound prepared in Example 60, 5 ml ethanol and 34 mg sodium borohydride. Remove the solvent (ethanol) with nitrogen. Add water and methylene chloride and partition. Wash with water then brine and dry over sodium sulfate to recover the title compound.

Prepare the hydrochloride salt by reaction with 1.05 eq. of 0.1N HCl.

FAB/Gly-Thio-MS: m/z 337 (M$^+$) HCl salt.

EXAMPLE 64

N-[6-(1-imidazolyl)hexanoyl]-1-adamantanamine (a) Stir for 0.5 hours at 0° C. in a reaction flask, 9.5 gm adamantanamine and 12 gm 6-bromohexanoyl chloride in 200 ml THF. Remove the THF and partition with methylene chloride/water then methylene chloride/5% HCl, then methylene chloride/5% sodium carbonate and finally methylene chloride/water to yield 6-(1-adamantanamine)-6-oxohexyl-1-bromide.

(b) Add 1 gm of the compound produced in Example 64(a) and 2 gms sodium imidazole to 25 ml DMF, stir overnight at room temperature. Remove the solvent under vacuum. Partition with 100% methylene chloride then 5% methanol/methylene chloride to yield the title compound.

Prepare the hydrochloride salt by reaction with 0.1N HCl.

EXAMPLE 65

1-[6-(5-chloro-2-methoxy-4-methyl-phenyl)hexyl]imidazole and 1-[6-(3-chloro-6-methoxy-2-methylphenyl)hexyl]imidazole (a) Add 1 gm of 2-chloro-5-methoxytoluene to 50 ml THF, cool to about −8° C. then add 4.5 ml of n-butyl lithium 2.5M in hexane, allow to warm to about 10° C. then add to a cool solution of 10 gm of 1,6-dibromohexane and 2.25 gms potassium teritary butoxide in 50 ml THF. Stir for 0.5 hr. then warm to room temperature. Stir overnight, cool and remove the solvent. Partition with water/methylene chloride to yield 1-[6-(5-chloro-2-methoxy-4-methylphenyl)hexyl] bromide mixed with 1-[6-(3-chloro-6-methoxy-2-methylphenyl)hexyl]bromide, boiling point 120°–140° C. at 0.05 mm Hg.

(b) Add 1.7 gm of the mixture prepared in step (a) to 3 gms sodium imidazole in 25 ml DMF and stir overnight. Remove the solvent and partition with water/methylene chloride. Elute on a silica column with 100% methylene chloride then 10% methanol to give a mixture of the title compounds which are separated by HPLC chromatography.

Prepare the hydrochloride salts of the title compounds by reaction with 1.1 eq. of 0.1N HCl.

EXAMPLE 66

1-[6-oxy-6-(4-methoxyphenyl)hexyl]imidazole (a) Add 1.1 gm anisole to 2.2 gm 1-bromohexanoyl chloride in 100 ml methylene chloride. Add 1.5 gm aluminum chloride and stir for 45 mins. Partition with water, 5% NaHCO$_3$ and water. Remove solvent and recover 1-[6-oxy-6-(4-methoxyphenyl)hexyl]bromide.

(b) Stir for 48 hours at room temperature 2.6 gms of the compound produced in step (a) and sodium imidazole (4 eq.) in 25 ml DMF. Partition with water/methylene chloride. Remove the solvent. Elute on a silica column with 100% methylene chloride then 5% methanol to obtain the title compound.

Prepare the hydrochloride salt by reaction with 0.1N HCl.

EXAMPLE 67

1-[6-oxy-6-(2,4-dimethoxyphenyl)hexyl]imidazole (a) Add 1.4 gm 2,4-dimethoxybenzene and 2.2 gm 1-bromohexanoyl chloride to 100 ml methylene chloride. Add 1.3 ml tin chloride and stir for 0.5 hr. Wash with water then 5% sodium bicarbonate to yield 1-[6-oxy-6-(2,4-dimethoxyphenyl)hexyl]bromide.

(b) Add 2.8 gm sodium imidazole in DMF to 3 gm of the compound produced in step (a). Stir for 48 hours, remove DMF, partitition with water/methylene chloride, elute on silica column with 100% methylene chloride then 5% methanol/methylene chloride to yield the title compound.

Prepare the hydrochloride salt by reaction with 0.1N HCl.

EXAMPLE 68

1-[6-hydroxy-6-(2,4-dimethoxyphenyl)hexyl]imidazole

Add 50 ml of ethanol to 1.3 gm of the compound prepared in Example 67, then add 0.5 gm sodium borohydride. Stir for 2.5 hours, remove the solvent, extract with methylene chloride, elute on a silica column with 100% methylene chloride, then 5% methanol/methylene chloride to yield the title compound.

EXAMPLE 69

1-[6-(2,4-dimethoxyphenyl)hex-5-enyl]imidazole, hydrochloride

Treat 0.266 gm of the compound prepared in Example 68 with 11 ml of 0.1N HCl to give the title compound.

EXAMPLE 70

1-[6-oxy-6-(2-chloro-4-methoxyphenyl)hexyl]imidazole (a) Add 2.85 gm of meta-chloroanisole to 4.5 gm 1-bromo-hexazoyl chloride in 200 ml methylene chloride. Add 3.2 gm aluminum chloride and stir for 2.5 hours. Add water and stir overnight. Partition with water/methylene chloride, then 5% sodium bicarbonate/methylene chloride. Elute on a silica column with hexane, then methylene chloride to yield 1-[6-oxy-6-(2-chloro-4-methoxyphenyl)hexyl]bromide.

(b) Add 1.5 gms of the compound prepared in step (a) to sodium imidazole prepared from 2.8 gms imidazole and 0.8 mg sodium hydroxide in 25 ml DMF and stir overnight. Remove the solvent then partition with methylene chloride/water. Elute on a silica column with 100% $CH_2Cl_2$ then 5% methanol/methylene chloride to yield the title compound and as a side product pentyl, para, meta, chloroanisole ketone.

Prepare the hydrochloride salt by reaction with 0.1N HCl.

EXAMPLE 71

1-[6-hydroxy-6-(4-methoxyphenyl)hexyl]imidazole

Add to 1 gm of the title compound prepared in Example 66 in 50 ml ethanol, 0.5 gm sodium borohydride, stir for 2.5 hours then remove the solvent. Extract with methylene chloride. Elute on a silica column with 100% methylene chloride then 5% methanol/methylene chloride to yield the title compound.

EXAMPLE 72

1-[6-(4-methoxyphenyl)hex-5-enyl]imidazole, hydrochloride

Add 0.529 gms of the compound prepared in Example 71 to 22 ml 0.1N HCl to yield the title compound.

EXAMPLE 73

1-[6-hydroxy-6-(2-chloro-4-methoxyphenyl)hexyl]imidazole

Add 25 ml ethanol to 300 mg of the title compound prepared in Example 70, then add 400 mg sodium borohydride, stir for 2 hours. Remove the solvent. Partition with water/methylene chloride. Elute the methylene chloride residue on a silica column with 100% methylene chloride then 5% methanol/methylene chloride to yield the title compound.

EXAMPLE 74

1-[6-(4-methoxyphenyl)hexyl]imidazole

Add 1 ml water to 400 mg of the compound prepared in Example 72, then add 100 mg sodium bicarbonate followed by 25 ml ethanol. Add 100 mg PtO and add hydrogen under 30 psi for 20 hr. Partition with water/methylene chloride. Elute on a silica column with 100% methylene chloride then 5% methanol/methylene chloride to yield the title compound.

Prepare the hydrochloride salt by reaction with 0.1N HCl.

EXAMPLE 75

1-[6-(naphthalene-2-oxy)hexyl]imidazole (a) Add 5 gm of beta-naphthol to 100 ml methylene chloride then add 27 ml 1,6-dibromohexane followed by 0.5 gm tetra n-butyl ammonium sulfate then 75 ml water and 25 ml of 50% sodium hydroxide. Stir for 48 hours, partition with water/methylene chloride, remove the methylene chloride and distill the residue at 0.1 mm mercury to give the product 1-[6-(naphthalene-2-oxy)hexyl]bromide.

(b) Add 2 gm of the compound produced in step (a) to a solution of 2 gm imidazole and 0.5 gm sodium hydroxide in 20 ml DMF and stir overnight. Remove the solvent, partition with methylene chloride/water. Elute on a silica column with 100% methylene chloride then 5% methanol to yield the title compound.

Prepare the hydrochloride salt by reaction with 0.1N HCl.

EXAMPLE 76

1-[6-(4-methylthiophenoxy)hexyl]imidazole (a) Add 10 gm 4-methylthiophenol and 1,6-dibromohexane to 200 ml methylene chloride, and 150 ml water, then 2 gm tetra n-butyl ammonium sulfate and 50 ml of 50% NaOH solution. Stir overnight, wash with water then brine, remove methylene chloride and distill off excess dibromohexane at 70° C. and 0.1 mm mercury in a 90° C. temperature bath. Crystallize the resulting compound, 1-[6-(4-methylthiophenoxy)hexyl]bromide, from hexane.

(b) Dissolve 1.5 gm sodium hydroxide and 5 gm imidazole in DMF. Add 5 gm of the compound prepared in step (a) and stir 48 hours. Remove the solvent, partition with water/methylene chloride. Elute on a silica column with 100% methylene chloride then 5% methanol to obtain the title compound.

Prepare the hydrochloride salt by reaction with 0.1N hydrochloric acid.

EXAMPLE 77

1-[6-(4-methylsulfonylphenoxy)hexyl]imidazole

Add 1 gm of the title compound prepared in Example 76 to 50 ml acetic acid. Then add 6 ml of 30% hydrogen peroxide. Stir for 3 hours. Add 6 ml more of 30% hydrogen peroxide and stir overnight. Add sufficient 15% sodium hydroxide to adjust the pH to 11. Partition with methylene chloride/water. Remove methylene chloride and recover the title compound.

Prepare the hydrochloride salt by reaction with 0.1N hydrochloric acid.

EXAMPLE 78

1-[6-(4-methoxyphenylthio)hexyl]imidazole (a) Add to a reaction flask 10 gm p-mercaptoanisole, 55 ml 1,6-dibromohexane, 150 ml water, 200 ml methylene chloride, 50 ml of 50% sodium hydroxide and finally 2 gm tetra n-butylammonium sulfate and stir overnight. Partition with water/methylene chloride then brine/methylene chloride. Remove excess dibromohexane. Add the resulting residue to hexane, remove crystalline disulfide side product then remove the hexane to obtain 1-[6-(4-methoxyphenylthio)hexyl]bromide.

(b) Dissolve 5 gm imidazole and 1.5 gm sodium hydroxide in DMF. Add 5 gms of the compound prepared in step (a) and stir overnight. Remove the solvent, partition with water/methylene chloride. Elute the methylene chloride. Elute the methylene chloride fraction on a silica column with 100% methylene chloride then with 5% methanol/methylene chloride to yield the title compound.

Prepare the hydrochloride salt by reaction with 0.1N hydrochloric acid.

EXAMPLE 79

1-[6-(4-methoxyphenylsulfonyl)hexyl]imidazole

Add 3.5 gm of the title compound prepared in Example 78 to 125 ml acetic acid, then add 24 ml of 30% hydrogen peroxide in 2 portions, 24 hours apart, stir for 8 hours. Adjust pH to >10 with 25% sodium hydroxide. Partition with water/methylene chloride. Elute on a silica column using 100% methylene chloride then 5% methanol to yield the title compound.

Prepare the hydrochloride salt by reaction with 0.1N hydrochloric acid.

EXAMPLE 80

1-[7-(2-chloro-4-methoxyphenoxy)octyl]imidazole hydrochloride (a) Combine sodium imidazole (5 g) and 8-bromo-1-octene (5 g) in DMF and stir overnight. Partition the reaction product between water and dichloromethane, evaporate the organic layer and purify the resultant residue on a silica gel column. Add the imidazole compound (4.6 g) and phenol (1 g) to dichloromethane (250 ml), saturate the solution with HBr gas and stir for 4 hours. Evaporate the solvent and wash the residue with THF: hexane (1:1) to obtain 1-(2-bromooctyl)imidazole hydrobromide.

(b) Combine the product of step (a) (2 g) with sodium iodide (30 g) in 2-butanone (100 ml) and reflux for 1 hour. Evaporate the solvent and extract the resultant residue with dichloromethane. Evaporate the solvent to obtain 1-(2-iodooctyl)imidazole hydrochloride.

(c) Combine the product of step (b) (2.5 g) with 2-chloro-4-methoxyphenol (5.2 g) and potassium carbonate (10 g) in acetone (100 ml) and relux for 48 hours. Evaporate the solvent, extract the resultant residue with dichloromethane and purify on a silica gel column, eluting with 100% $CH_2Cl_2 \rightarrow 10\%$ $CH_3OH/CH_2Cl_2$.

EXAMPLE 81

N-(2-chloro-4-methylphenyl)-6-(1H-1-imidazolyl) hexanamide hydrochloride

Add 2-chloro-4-methylaniline (1 g) to THF (10 ml) and add, at room temperature over 15 min., an aqueous NaOH solution (0.338 g NaOH in 5 ml water) and 6-bromohexanoyl chloride (1.08 ml). Stir at 1 hour at room temperature, add NaCl (2 g), separate the organic layer and evaporate the solvent to obtain a solid.

Combine the above reaction product with imidazole (3 eq.) and NaOH (3 eq.) in DMF (25 ml) and stir overnight. Extract the resultant mixture with dichloromethane and wash with water. Isolate the product from a silica gel column, eluting with $CH_2Cl_2$, 2% MeOH in $CH_2Cl_2$, then 3% MeOH is $CH_2Cl_2$. Prepare the hydrochloride salt with 1 eq. of 0.1N HCl. MS: m/z 306 (M+).

EXAMPLE 82

N-(2-chloro-4-methylphenyl)-N-methyl-6-(1-imidazolyl)-1-hexanamine hydrochloride (a) Add 2-chloro-4-methyl aniline (3 g) to THF (30 ml), then over a period of 30 min. add NaOH (1.02 g) in water (15 ml) and 6-bromohexanoyl chloride (324 ml) and stir 2 hours. Add NaCl, separate the organic layer and evaporate the solvent obtain a solid.

Add the resultant solid (2 g) to freshly distilled THF (40 ml) and 50% sodium hydride/oil (0.425 g). Stir 30 min. add iodomethane (4.56 g) and stir for 2.5 hours. Evaporate the THF, add dichloromethane, wash with water and dry the organic layer over $Na_2SO_4$. Purify on a silica gel column, eluting with dichloromethane.

(b) Combine the product of step (a) (1.5 g) with sodium imidazole (1.215 g) in DMF (15 ml) and stir overnight. Extract the resultant mixture with dichloromethane, wash with water and evaporate the organic layer.

(c) Dissolve the product of step (b) (0.5 g) in THF which has been filtered through alumina (10 ml), add lithium aluminum hydride (0.30 g) and stir overnight. Reduce the volume by evaporating THF under $N_2$, add water slowly and extract (3×) with dichloromethane. Evaporate the solvent and purify the resultant residue on a silica gel column, eluting with $CH_2Cl_2$, 3% MeOH in $CH_2Cl_2$, then 5% MeOH in $CH_2Cl_2$. Prepare the hydrochloride salt of the title compound by reacting with about 1 eq. of 0.1N HCl. MS: m/z 306 (M+).

EXAMPLE 83

N-(2-chloro-4-methylphenyl)-N-methyl-6-(1-imidazolyl)hexanamide hydrochloride

Add about 1 eq. of 0.1N HCl to the product of Example 82, step (b) and lyophilize overnight to obtain the title compound, MS: m/z 320 (M+).

EXAMPLE 84

N-(2-chloro-4-methylphenyl)-6-(1-imidazolyl)-1-hexanamine hydrochloride

Dissolve the product of Example 81 (0.448 g) in anhydrous THF (10 ml) and add, in one portion, lithium aluminum hydride (0.230 g). Stir for 2 hours, then let stand for 60 hours, extract with dichloromethane and wash with water. Evaporate the organic solvent and purify the resultant residue on a silica gel column, eluting with $CH_2Cl_2$, 1% MeOH/$CH_2Cl_2$.

Add about 1 eq. of 0.1N HCl and lyophilize to obtain the title compound, MS: m/z 292 (M+).

EXAMPLE 85

1-[6-(3,5-dimethoxybenzyloxy)hexyl]imidazole hydrochloride (a) Combine imidazole (10 g) and 1,6-dibromohexane (60 ml), stir for 1 hour, add 12 N HCl (25 ml), evaporate the solvent and extract the resultant residue with hexane. Partition the resiude with water:ethyl acetate, add NaOH to adjust the aqueous layer to pH 11 and extract the aqueous layer with dichloromethane. Evaporate the solvent and purify the resultant residue on a silica gel column, eluting with 100% $CH_2Cl_2$→100% ethyl acetate. Add trifluoroacetic acid to the desired fractions and evaporate the solvent to obtain 1-(6-bromohexyl)imidazole trifluoracetate.

(b) Combine 3,5-dimethoxybenzyl alcohol (1.94 g) and powdered NaOH (0.695 g) in DMF (20 ml) and stir to dissolve. Add the product of step (a) (1 g) and stir 60 hours. Evaporate the solvent, extract the resultant residue with dichloromethane, wash the organic layer sucessively with 10% aqueous NaOH, water and brine, then dry over $Na_2SO_4$ and evaporate the organic solvent. Purify on a silica gel column, eluting with $CH_2Cl_2$→1,2 and 3% MeOH/$CH_2Cl_2$.

Prepare the hydrochloride salt by reacting with about 1 eq. of 0.1N HCl. MS: m/z 318 (M+).

EXAMPLE 86

2(R)-[2-(2-chloro-4-methoxyphenoxy)ethyl]-3(R),4(S)-dihydroxy-5(R)-(1-imidazolylmethyl)-tetrahydrofuran hydrochloride (a) Dissolve ribofuranose tetraacetate (10 g) in dry dichloromethane (100 ml), add allyltrimethyl silane (15 ml) and boron trifluoroetherate (11.02 ml) and stir overnight. Evaporate the solvent and purify the resultant residue on silica gel, eluting with 20%, 30 and 40% EtOAc/hexane.

Cool to –78° C. a solution of the resultant residue (3 g) in dichloromethane (50 ml), bubble in ozone, continuing to bubble ozone for 10 min. after a constant blue color is obtained, then purge with $N_2$. Add methyl sulfide (20 ml) and let stand overnight, add more methyl sulfide (15 ml), warm until boiling, then let cool and stir 1 hour. Evaporate the solvent, extract the resultant residue with dichloromethane, wash with 40% saturated brine/water, dry the organic layer over $Na_2SO_4$ and evaporate the solvent. To the resultant residue add THF (100 ml), acetic acid (12 ml) and ground sodium cyanoborohydride (7.5 g) and stir overnight. Evaporate the solvent, add dichloromethane and purify on a silica column.

Cool to 0° a solution of the above residue (1 g) in THF (30 ml), add mesyl chloride (0.747 ml) and triethylamine (1.345 ml) and stir overnight. Evaporate the solvent, extract the resultant residue with dichloromethane, wash with water, dry the organic layer over $Na_2SO_4$ and evaporate the solvent. Add to the resultant residue (1.28 g) in DMSO (115 ml) sodium 2-chloro-4-methoxyphenolate (1.8 g) and stir overnight. Extract resultant mixture with dichloromethane, wash with water and dry the organic layer over $Na_2SO_4$. Evaporate the solvent and purify the resultant residue on a silica column, eluting with $CH_2Cl_2$→3%, 5% and 8% EtOAc/$CH_2Cl_2$.

Add the above product (1.02 g) to methanol (20 ml), add potassium carbonate (0.317 g) and stir for 3.5 hours. Evaporate the solvent under $N_2$ and high vacuum. Dissolve the residue in water, add salt, extract with dichloromethane and evaporate the solvent.

Cool to 0° a solution of the resultant residue (0.270 g) in THF (5 ml), add methane sulfonyl chloride (0.097 g) and triethylamine (0.085 g), let warm to room temperature and stir for 2.5 hours. Evaporate the solvent, extract the residue with dichloromethane, wash with water, then brine, dry over $Na_2SO_4$ and evaporate the solvent. Purify the resultant residue on a silica column, eluting with $CH_2Cl_2$→20%, 25%, 30%, 40% and 50% EtOAc/$CH_2Cl_2$ to obtain 2(R)-[2-(2-chloro-4-methoxyphenoxy)ethyl] -3(R),4(S)-dihydroxy-5(R)-(methylsulfonyloxymethyl)-tetrahydrofuran.

(b) To a solution of the product of step (a)(0.175 g) in DMF (3.5 ml). add sodium imidazole (0.238 g) and stir at 50° (oil bath) overnight. Reduce volume of DMF under $N_2$ with mild heating. Extract the residue with dichloromethane and wash with brine. Evaporate the solvent and purify the residue on a silica column, eluting with $CH_2Cl_2$→3%,6% and 9% MeOH/$CH_2Cl_2$. MS: m/z 369 (M+), $[\alpha]_D$ =+47.9 (1% in MeOH, 1 ml cell).

Combine 50 mg of the product of step (b) and 4.9 mg hydrochloric acid and lyophilize to obtain the title compound. FAB/Gly-Thio-MS: m/z 369 (M+), HCl salt.

EXAMPLE 87

2(R)-[2-(2-chloro-4-methoxyphenoxy)ethyl]-3(R),4(S)-dihydroxy-5(R)-[1-(1,2,4-triazolylmethyl)]tetrahydrofuran To a solution of the product of Example 86, step (a) (0.20 g) in DMF (4 ml), add 1,2,4-triazole (0.139 g) and NaOH (0.080 g) and stir overnight at 70° C. (oil bath). Evaporate DMF under $N_2$ at 70° C., slurry the residue in dichloromethane, filter and charge to a silica column, eluting with $CH_2Cl_2$→3%,5% and 8% MeOH/$CH_2Cl_2$. FAB/Gly-Thio-MS: m/z 370 (M+), $[\alpha]_D$=+46.7 (1% in MeOH, 1 ml cell)

EXAMPLE 88

2(S)-[2-(2-chloro-4-methoxyphenoxy)ethyl]-5(S)-(1-imidazolylmethyl)tetrahydrofuran hydrochloride (a) Combine the product of Example 86, step (a) (2.37 g) in dichloromethane (20 ml) with trimethylorthoformate (3.92 ml) and pyridinium p-toluene sulfonate (12.1 ml) and stir overnight at room temperature. Wash the reaction mixture with NaHCO$_3$, water and brine, then dry over Na$_2$SO$_4$ and evaporate the solvent. Purify the resultant residue on a silica column with 25% EtOAc/hexane→40% EtOAc/hexane.

Add the resultant product (2.1 g) to acetic anhydride (50 ml) and heat in an oil bath at 140° C. for 20 hours. Evaporate the solvent, dissolve the residue in dichloromethane, add saturated aqueous NaHCO$_3$ and stir for 2 hours. Remove the organic layer, wash it with water and brine, dry over Na$_2$SO$_4$ and purify on a silica column, eluting with 10% EtOAc/CH$_2$Cl$_2$.

(b) Combine the product of step (a) (1.55 g) in DMF (15 ml) with sodium imidazole (1.92 g) and stir for 60 hours, then heat at 60° C. (oil bath) for 4 hours. Evaporate the solvent, dissolve the resultant residue in dichloromethane, wash with water and brine, then dry over Na$_2$SO$_4$. Purify the resultant residue on a silica column, eluting with CH$_2$Cl$_2$→20% EtOAc/CH$_2$Cl$_2$→15% MeOH/CH$_2$Cl$_2$. $[\alpha]_D$=+104.33, 1% in CHCl$_3$, 100 mm cell; MS: m/z 335 (M+1).

(c) Hydrogenate the product of step (b) (100 mg) with PtO (40 mg) in EtOH (25 ml) in a Paar shaker at 30 psi H$_2$ overnight. Filter the resultant mixture through celite, wash with ethanol and evaporate the solvent. Add 1 eq. of 0.1N HCl and lyophilize to obtain the title compound, $[\alpha]_D$=+27.6, 1% in CHCl$_3$, 100 mm cell.

EXAMPLE 89

2(S)-[2-(2-chloro-4-methoxyphenoxy)ethyl]-5(S)-(1-imidazolylmethyl)-2,5-dihydrofuran hydrochloride Combine the product of Example 88, step (b) (0.10 g) with 3.58 ml of 0.1N HCl and lyophilize overnight to obtain the title compound. MS: m/z 335 (M+1).

EXAMPLE 90

2(R)-[2-(2-chloro-4-methoxyphenoxy)ethyl]-3(R),4(S)-dihydroxy-5(R)-2,4-dioxo-1,2,3,4-tetrahydropyrimidin-1-yl)methyl tetrahydrofuran (a) To a solution of ribofuranose tetraacetate (50 g) in methylene chloride (500 ml), add allyltrimethyl silane (539 g) and BF$_3$ etherate (57.9 ml). Let stir overnite. Remove solvent and chromatograph on a silica gel column, eluting with 20% EtOAc/Hexane→30% EtOAc/Hexane→40% EtoAc/Hexane. Stir the resultant isolated product (49.5 g) for 2 hours in methanol (500 ml) containing potassium carbonate (68.9 g). Filter potassium carbonate and remove the solvent. Add 12 N. HCl (20 ml) and acetone (80 ml) and stir 10 mins. to dissolve. Add more acetone (500 ml) and stir 2 hours. Add potassium carbonate (3 eq.) and let stir overnite. Filter off excess potassium carbonate and remove acetone. Add CH$_2$Cl$_2$ (300 ml) and wash with H$_2$O, then brine. Remove solvent and chromatograph on silica gel, eluting with 20% EtOAc/Hexane.

(b) Combine the product of step (a) (1.0 g), dichloromethane (50 ml) and triethylamine (1.063 ml) and add over 35 min. by syringe pump methane sulfonyl chloride (0.577 ml) in dichloromethane (13.8 ml). Stir 3 hours, wash with water and dry the dichloromethane solution over Na$_2$SO$_4$. Cool the solution to −78° C., bubble ozone until a blue color appears and immediately purge with N$_2$. Reduce the volume of the solution, add methyl sulfide (30 ml) and reflux for 4 hours. Evaporate the solvent, add DMF (30 ml) to the resultant residue, add 5% aqueous NaHCO$_3$ (25 ml) and excess sodium borohydride and stir for 2 hours. Evaporate the solvent and extract the residue with dichloromethane.

To diisopropyl azodicarboxylate (0.172 ml), triphenyl phosphine (0.229 g) and 2-chloro-4-methoxyphenol (0.149 g), add the product of the above paragraph (0.20 g) in THF (3 ml) and stir overnight. Evaporate the solvent under N$_2$, extract the residue with dichloromethane, wash with 10% aqueous NaOH, water and brine and dry over Na$_2$SO$_4$. Purify the product on a silica column, eluting with 25% EtOAc/hexane→40% EtOAc/hexane.

Dissolve the above mesylate (0.20 g) in DMF (5 ml), add 2N-benzoyl uracil (0.396 g) and cesium carbonate; stir for 60 hours; heat at 60° C. (oil bath) overnight, add methanol (10 ml) and heat at 50°–60° C. for 1 hour, then let stand overnight. Extract with dichloromethane, wash with water and purify on a silica column.

Combine the above residue (0.095 g) with methanol (4 ml), water (1 ml) and concentrated HCl (5 drops). Stir overnight, then add excess potassium carbonate and again stir overnight. Evaporate the solvent, add EtOAc and water separate and evaporate the organic layer to obtain the title compound. $[\alpha]_D$= +90.2, 1% in MeOH, 1 ml cell; FAB/Gly-Thio -MS: m/z 413 (M+1).

EXAMPLE 91

4(R)-[2-(2-chloro-4-methoxyphenoxy)methyl-6(R)-[2(2,4-dioxo-1,2,3,4-tetrahydropyrimidin-1-yl)ethyl]2,2-dimethyl-3a,4,6,6a-tetrahydro-3a(R),6a(S)-furo-[3,4-d]-1,3-dioxole (a) Treat ribofuranose tetracetate as described in Example 86(a), first paragraph. Add the product (4.5 g) to methanol (50 ml), add potassium carbonate (1 g) and stir overnight. Filter and evaporate the solvent, add acetone (50 ml) and conc. HCl (1 ml) to pH 1, stir 6 hours, add sodium bicarbonate, stir 15 min. and filter. Evaporate the solvent and purify the resultant residue on a silica column, eluting with 100% hexane→50% EtOAc To the resultant acetonide, add dichloromethane (50 ml) and triethylamine (0.9 ml), cool to 0° C., and add methane sulfonyl chloride (0.45 ml) by syringe pump over 45 min. Wash the reaction mixture with water and evaporate the solvent.

Add the resultant residue (1.5 g) and sodium 2-chloro-4-methoxyphenolate (2 g) to DMSO (25 ml) and stir overnight. Partition the product with water/dichloromethane, separate the organic layer and evaporate the solvent. Purify the resultant residue on a silica column, eluting with hexane-→20% EtOAc/hexane.

Cool to −78° C. a solution of the above product in dichloromethane (100 ml) and bubble ozone until a blue color appears, then purge with N$_2$ and warm to room temperature. Evaporate the solvent, add ethanol (50 ml) and sodium borohydride (1 g) and stir 5 hours. Evaporate the solvent and partition the resultant residue between water-dichloromethane. Purify the product on a silica column, eluting with CH$_2$Cl$_2$→EtOAc.

Dissolve the above product in dichloromethane, cool to 0° C. and add triethylamine (0.7 ml), then add methane sulfonyl chloride (0.36 ml) in dichloromethane (10 ml) by syringe pump over 25 min. Stir for 15 min., wash with water and evaporate the solvent to obtain 4(R)-(2 -chloro-4-methoxyphenoxy)-methyl-6(R)-[2-(methylsulfonyloxy)ethyl] -2,2- dimethyl-3a,4,6,6a-tetrahydro- 3a (R), 6a(S)-furo[3,4-d]-1,3-dioxole.

(b) Combine the product of step (a) (0.240 g) in DMF (5 ml) with 2N-benzoyl uracil (0.475 g) and cesium carbonate (0.492 g). Stir for 4 days and purify the resultant product on a silica column, eluting with $CH_2Cl_2 \rightarrow 20\%$, 30% and 40% $EtOAc/CH_2Cl_2 \rightarrow EtOAc$ to obtain the title compound, FAB/Gly-Thio-MS: m/z 453 (M+1).

EXAMPLE 92

2(R)-(2-chloro-4-methoxyphenoxy)methyl-3(R),4(S)-dihydroxy-5(R)-[
2-(2,4-dioxo-1,2,3,4-tetrahydropyrimidin-1-yl)ethyl]tetrahydrofuran Treat the compound prepared in Example 91 in a manner similar to that described in the last paragraph of Example 90, step (b) to obtain the title compound, $[\alpha]_D=+49.9$, 1% in MeOH, 1 ml cell; FAB/Gly-Thio-MS: m/z 413 (M+1).

EXAMPLE 93

5(R)-[2-(1-imidazolyl)ethyl]-3(R),4(S)-dihydroxy-2(R)-(2-chloro-4
-methoxyphenoxy)methyltetrahydrofuran hydrochloride Combine the product of Example 91, step (a)(0.125 g) and sodium imidazole (0.5 g) in DMF (5 ml) and stir for 72 hours. Evaporate the solvent and partition the resultant residue with water-dichloromethane. Evaporate the solvent and purify the residue on a silica column, eluting with 50% $EtOAc/CH_2Cl_2 \rightarrow EtOAc \rightarrow 10\%$ $CH_3OH/CH_2Cl_2$.

Add 15 ml 0.1N HCl to the product (100 mg) and let stand 72 hours at room temperature. Lyophilize to obtain the title compound, $[\alpha]_D=+22.4$, 1% in $CH_3OH$, 10 cm cell.

EXAMPLE 94

2(R)-[2-(2-chloro-4-methoxyphenoxy)ethyl](R),
4(S)-dihydroxy-5(R)-(2-chloro-4-methoxyphenoxy)methyl tetrahydrofuran Add the product of Example 91, step (a) (0.20 g) and sodium 2-chloro-4-methoxyphenolate (0.350 g) to DMSO (15 ml) and stir overnight. Partition with water/dichloromethane, evaporate the organic layer and purify the resultant residue on a silica column, eluting with $CH_2Cl_2 \rightarrow EtOAc$.

Heat the above product to 80° C. in 80% acetic acid overnight. Partition the resultant product with water/dicloromethane and purify on a silica column to obtain the title compound, $[\alpha]_D=+26.7$, 1% in methanol.

EXAMPLE 95

2(R)-[2-(adenin-7-yl)ethyl]-3(R),4(S)-dihydroxy-
5(R)-(2-chloro-4-methoxyphenoxy) methyl
tetrahydrofuran To benzoyl adenine (1 g) in DMF (10 ml), add sodium hydride (50/50 in oil) (0.225 g) and stir. Add the product of Example 91, step (a)(0.5 g) in DMF (10 ml) and stir, then heat to 50° C. for 18 hours. Remove the DMF under high vacuum, partition the residue with $CH_2Cl_2$/water, separate the organic layer and evaporate the solvent. Purify the resultant residue on a silica column, eluting with 100% EtOAc to give a mixture of isomers.

To the mixture, add methanol (25 ml) and potassium carbonate (3 g) and stir overnight. Evaporate the solvent, extract with water/$CH_2Cl_2$ and purify the resultant residue on a silica column, eluting with EtOAc to obtain 2 fractions.

Heat a solution of the more polar fraction in 85% aqueous acetic acid for 24 hours. Remove the solvent under $N_2$ and purify the resultant residue on a silica column, eluting with $CH_2Cl_2 \rightarrow 10\%$ $MeOH/CH_2Cl_2$ to obtain the title compound, $[\alpha]_D=+35.2$, 1% in MeOH.

EXAMPLE 96

5(R)-(2-chloro-4-methoxyphenoxy)methyl-
3(R),4(S)-dihydroxy-2
(R)-[2-(N-benzimidazolyl)ethyl]tetrahydrofuran Combine the product of Example 91, step (a) (0.20 g) and benzimidazole (0.20 g) in DMSO (10 ml), add cesium carbonate (0.70 g) and stir 48 hours. Partition the product with $CH_2Cl_2$/water, evaporate the solvent and purify the resultant residue on a silica column, eluting with $CH_2Cl_2 \rightarrow$ EtOAc.

Dissolve the above product (0.150 g) in 85% aqueous acetic acid (10 ml) and reflux overnight. Remove solvent under $N_2$, add methanol (20 ml) and potassium carbonate (2 g) and stir for 2 hours. Evaporate the solvent and purify the resultant residue on a silica column, eluting with $EtOAc \rightarrow 5\%$ $CH_3OH/EtOAc$ to obtain the title compound, $[\alpha]_D=+36.1$, 1% in MeOH.

EXAMPLE 97

5(S)-[2-(1-imidazolyl) ethyl]-3(R),4(S)
-dihydroxy-2(R)-(2-chloro- 4-methoxyphenoxy)
methyltetrahydrofuran hydrochloride (a) Dissolve ribose acetonide (150 g) in dichloromethane (2.5), add $P_2O_5$ (113 g) and stir for 2 hours. Add celite and filter, wash with 2.5% aqueous NaOH(1/1), then water, dry and filter through silica. Purify the product on a silica column, eluting with hexane$\rightarrow$50% EtOAc/hexane.

Add the resultant residue (48 g) to acetonitrile (50 ml), add allyltrimethyl silane (200 ml) and cool to −78° C. Add trimethylsilyloxytriflate (240 ml), warm to room temperature and stir overnight. Pour the reaction mixture into 500 g ice, stir for 15 min. and separate the layers; wash the aqueous layer 3× with dichloromethane, saving and combining the organic layers. Evaporate the water, extract the residue with acetone, filter and adjust volume to 1/1 with acetone. Add conc. HCl (10 ml), stir overnight, then neutralize with potassium carbonate. Evaporate the solvent, extract the residue with $CH_2Cl_2$:hexane (1:1) and evaporate the solvent. To the combined dichloromethane layers from above, add methanol (500 ml), water (50 ml) and conc. HCl (20 ml), stir overnight and add potassium carbonate to neutralize. Evaporate the solvent, partition with $CH_2Cl_2$/water and evaporate aqueous layer to obtain a residue. Extract the residue with acetone, stir, neutralize and extract as above. Combine the crude products and purify by HPLC (silica, 20/80 EtOAc/hexane). $[\alpha]_D=-9.1$, 1% in $CHCl_3$. Treat the resultant cis isomer in a manner similar to that described in Example 91, step (a), paragraphs 2 to 5, to obtain 5(S)-[2-(1-methanesulfonate)ethyl] -2(R)-(2-chloro-4-methoxyphenoxy)methyl-2,2 -dimethyl-3a, 4,6,6a-tetrahydro-3a(R),6a(S)-furo-[3,4-d]-1,3-dioxole.

(b) Add the product of step (a) (0.150 g) and sodium imidazole (0.50 g) to DMF (5 ml) and treat in a manner similar to that described in Example 93 to obtain the title compound, $[\alpha]_D = -26.0$, 1% in MeOH, HCl salt.

EXAMPLE 98

2(R)-(2-chloro-4-methoxyphenoxy)methyl-3(R),4(S)-dihydroxy-5(S)-[2(N-benzimidazolyl)ethyl]tetrahydrofuran hydrochloride Treat the product of Example 97, step (a) in a manner similar to that described in Example 96, first paragraph.

Heat the resultant product (0.220 g) to 80° C. in 0.1N HCl (50 ml) for 4 hours; add NaOH to pH 11, saturate with NaCl; extract with dichloromethane, then EtOAc, combine the extracts and evaporate the solvent. React the resultant residue with 1 eq of 0.1N HCl and lyophilize to obtain the title compound, $[\alpha]_D = -21.1$, 1% in methanol, HCl salt.

EXAMPLE 99

(3 and 4)-hydroxy-5(S)-[2-(1-imidazolyl)ethyl]-2)(R)-(2-chloro-4-methoxyphenoxy)methyl-tetrahydrofuran hydrochloride (a) Combine 2(R)-(2-chloro-4-methoxyphenoxy)methyl]-3(R),4(S)-dihydroxy-5(S)-[2-(sulfonyl)ethyl] tetrahydrofuran (1.18 g) with trimethyl orthoformate (2 ml) and pyridinium tosylate (12.7 ml) in dichloromethane (10 ml) and stir for 24 hours. Evaporate volatiles with $N_2$, partition the resultant residue with water/dichloromethane and purify the dichloromethane residue on a silica column, eluting with EtOAc:hexane.

To the resultant product, add acetic anhydride (25 ml) and heat at 140° C. for 20 hours. Evaporate the solvent and purify the residue on a silica column, eluting with 25% EtOAc/hexane to obtain 5(S)-[2-(1-methane sulfonlyoxy]-2(R)-(2-chloro-4-methoxyphenoxy)-methyl-2,5-dihydrofuran.

(b) Combine the product of step (a) (0.645 g) and 3-chloroperoxybenzoic acid (1.6 g) in dichloromethane (5 ml) and stir overnight. Extract with dichloromethane, wash with 5% NaI, $Na_2S_2O_3$ and $NaHCO_3$, evaporate the dichloro-methane and purify the resultant residue on a silica plug, then a silica column, eluting with 25% and 50% EtOAc/hexane. Repeat purification on a silica column eluting with 30% EtOAc/hexane to isolate 2 isomers, A (less polar) and B (more polar).

Add isomer A (0.071 g) and NaI (1 g) to acetone (20 ml) and stir overnight. Evaporate the solvent, extract the resultant residue with dichloromethane, wash with resultant residue with dichloromethane, wash with dilute sodium thiosulfate and evaporate the organic layer. Treat isomer B (0.090 g) in a similar manner.

Combine the above product (isomer A) with sodium imidazole (0.10 g) in DMF (2 ml) and stir overnight. Partition the product with water/dichloromethane, then purify the resultant residue on a silica column, eluting with $CH_2Cl_2 \rightarrow 10\%$ $CH_3OH/CH_2Cl_2$. Treat isomer B in a similar fashion.

Add the product of the above paragraph (isomer A) to THF (5 ml), add superhydride (0.5 ml) and stir for 1 hour. Add 10% NaOH (1 ml) and hydrogen peroxide (1 ml of a 30% solution), stir for 1 hour and purify the resultant product on a silica column, eluting with $CH_2Cl_2 \rightarrow 10\%$ $CH_3OH/CH_2Cl_2$. MS: m/z 352 ($M^+ +1$). Treat isomer B in a similar manner (MS:m/z 352 ($M^+ +1$).

EXAMPLE 100

5(S)-[2-(1-imidazolyl)ethyl]-2(R)-(2-chloro-4-methoxyphenoxy)methyl-2,5-dihydrofuran hydrochloride Add sodium imidazole (0.05 g) to the product of Example 99, step (a) (0.10 g) in DMF (2 ml) and stir for 60 hours. Partition the product with water/dichloromethane, and evaporate the solvent to obtain the title compound, MS: m/z 337 ($M^+ +1$).

EXAMPLE 101

5(R)-[2-(1-imidazolyl)ethyl]-2(S)-(2-chloro-4-methoxyphenoxy)methyl-tetrahydrofuran, hydrochloride In a vial, add ethanol (1 ml) to the product of Example 100 (0.050 g) and add PtO (0.025 g). Place a balloon filled with $H_2$ gas over the mouth of the vial and stir overnight. Purify the resultant product on a silica column, eluting with $CH_2Cl_2 \rightarrow 5\%$ methanol/$CH_2Cl_2$. Add 0.1 N HCl (2 ml) to the resulting product and lyophilize to obtain the title compound, MS: m/z 339 ($M^+ +1$).

EXAMPLE 102

1-[6-(4-acetylphenoxy)hexyl]imidazole hydrochloride

Combine p-hydroxyacetophenone (3 g), acetone (60 ml), 1,6-dibromohexane (10.75 g) and potassium carbonate (6 g) and reflux for about 60 hours. Reduce the volume of acetone, add dichloromethane, extract with water and brine, dry over $Na_2SO_4$ and distill product at 0.05 mm, head temp. 175° C.

Add the distilled product (2 g) to DMF (20 ml), add sodium imidazole (1.8 g) and stir overnight. Extract the resultant product with dichloromethane, wash with water and brine, dry over $Na_2SO_4$, evaporate the solvent and purify the resultant residue on a silica column, eluting with $CH_2Cl_2 \rightarrow 1,2$ and 3% MeOH/$CH_2Cl_2$.

React the above product (0.125 g) with 1 eq. 0.1N HCl and lyophilize to obtain the title compound. FAB/Gly-Thio-MS: m/z 287 ($M^+ +1$), hydrochloride salt.

EXAMPLE 103

1-[6-(4-(1-hydroxyethyl)phenoxy)hexyl]imidazole hydrochloride

Add the product of Example 102 (0.20 g) to ethanol (10 ml), add sodium borohydride (0.053 g) and stir 3.5 hours. Reduce volume of ethanol under $N_2$, add dichloromethane, wash with water and brine, dry over $Na_2SO_4$ and evaporate the solvent. React the resultant product (0.02 g) with 1 eq. 0.1N HCl to obtain the title compound. FAB/Gly-Thio MS: m/z 289 ($M^+ +1$), hydrochloride salt.

EXAMPLE 104

1-[6-(4-carbamylphenoxy)hexyl]imidazole hydrochloride

In a manner similar to that described in Example 102, substitute 4-hydroxy benzamide for the acetophenone and add methanol during extraction to obtain the title compound, FAB/Gly-Thio-MS: m/z 288 ($M^+$+1), hydrochloride salt.

EXAMPLE 105

In a manner similar to that described in Example 85, substitute the following substituted phenols for the benzyl alcohol to obtain the compounds named below:

Substituted phenol:
(a) 2,4-dichlorophenol
(b) 4-chloro-3-methylphenol
(c) 2-chloro-5-methylphenol
(d) 2-chloro-4,5-dimethylphenol
(e) 4-chloro-3,5-dimethylphenol
(f) 2,4-difluorophenol
(g) 4-chloro-2-methylphenol
(h) 4-chloro-2,6-dimethylphenol
(i) 2-chloro-6-methylphenol
(j) 2-bromo-4-methylphenol
(k) 2,6-dichlorophenol Products:
(a) 1-[6-(2,4-dichlorophenoxy)hexyl]imidazole hydrochloride, MS: m/z 313 (M+1), hydrochloride
(b) 1-[6-(4-chloro-3-methylphenoxy)hexyl]imidazole hydrochloride, MS: m/z 293 ($M^+$+1), hydrochloride
(c) 1-[6-(2-chloro-5-methylphenoxy)hexyl]imidazole hydrochloride, MS: m/z 293 ($M^+$+1), hydrochloride
(d) 1-[6-(2-chloro-4,5-dimethylphenoxy)hexyl]imidazole hydrochloride, MS: m/z 307 ($M^+$+1), hydrochloride
(e) 1-[6-(3,5-dimethyl-4-chlorophenoxy)hexyl]imidazole hydrochloride, MS: m/z 307 ($M^+$+1)
(f) 1-[6-(2,4-difluorophenoxy)hexyl]imidazole hydrochloride, MS m/z 281 (M+1)
(g) 1-[6-(2-methyl-4-chlorophenoxy)hexyl]imidazole hydrochloride, MS: m/z 293 (M+1)
(h) 1-[6-(2,6-dimethyl-4-chlorophenoxy)hexyl]imidazole hydrochloride, MS: m/z 307 (M+1)
(i) 1-[6-(2-chloro-6-methylphenoxy)hexyl]imidazole hydrochloride, MS: m/z 293 (M+1)
(j) 1-[6-(2-bromo-4-methylphenoxy)hexyl]imidazole hydrochloride, MS: m/z 337 (M+1)
(k) 1-[6-(2,6-dichlorophenoxy)hexyl]imidazole hydrochloride, MS: m/z 313 ($M^+$+1)

EXAMPLE 106

1-[6-(2-chloro-5-hydroxyphenoxy)hexyl]imidazole (a) Add 6-(2-chloro-5-methoxyphenoxy)hexyl-1-iodide (10.020 g) and iodotrimethylsilane (0.10 g) to dichloromethane (100 ml) and reflux for 4 days. Evaporate the solvent and purify the resultant resiude on a silica column.

(b) Add imidazole (25 g) and NaOH (15 g) to DMF (250ml) and Stir for 1 hour. Add the product of part (a) (8.65 g) and stir overnight. Evaporate the solvent, partition the resultant residue with water/dichloromethane (adjust aqueous layer to pH 7 with potassium phosphate), separate organic layer and evaporate solvent. Purify the resultant residue on a silica column to obtain the title compound, MS: m/z 295 ($M^+$+1).

We claim:
1. A compound selected from the group consisting of:
2(R)-[2-(2-chloro-4-methoxyphenoxy)ethyl]-3(R),4(S)-dihydroxy-5(R)-(2,4-dioxo-1,2,3,4-tetrahydropyrimidin-1-yl)methyltetrahydrofuran;

2(R)-(2-chloro-4-methoxyphenoxy)methyl]-3(R),4(S)-dihydroxy-5(R)-[2-(2,4-dioxo-1,2,3,4-tetrahydropyrimidin-1-yl)ethyl]tetrahydrofuran;

1,3-di-[6-(2-chloro-4-methoxyphenoxy)hexyl]-1,2,3,4-tetrahydropyrimidine-2,4-dione;

1-[6-(2-chloro-4-methoxyphenoxy)hexyl]-1,2,3,4-tetrahydropyrimidine-2,4-dione; and 4(R)-[2-(2-chloro-4-methoxyphenoxy)methyl]-6(R)-[2-(2,4-dioxo-1,2,3,4-tetrahydropyrimidin-1-yl)ethyl]-2,2-dimethyl-3a, 4,6,6a-tetrahydro-3a(R), 6a(S)-furo-[3,4-d]-1,3-dioxole.

2. A pharmaceutical composition comprising, as the active ingredient, an antiviral effective amount of a compound according to claim 1 and a pharmaceutically acceptable carrier.

3. A method for treating viral infections comprising administering an anti-viral effective amount of a compound according to claim 1.

\* \* \* \* \*